(12) United States Patent
Adachi et al.

(10) Patent No.: US 6,214,873 B1
(45) Date of Patent: Apr. 10, 2001

(54) 2-AMINOPROPANE-1,3-DIOL COMPOUNDS, MEDICINAL USE THEREOF, AND INTERMEDIATES IN SYNTHESIZING THE SAME

(75) Inventors: Kunitomo Adachi, Fukuoka; Yoshiyuki Aoki, Hirakata; Tokushi Hanano, Fukuoka; Koji Teshima; Yukio Hoshino, both of Iruma; Tetsuro Fujita, Muko, all of (JP)

(73) Assignee: Welfide Corporation, Osaka (JP)

( * ) Notice: Subject to any disclaimer, the term of this patent is extended or adjusted under 35 U.S.C. 154(b) by 0 days.

(21) Appl. No.: 09/402,375

(22) PCT Filed: Apr. 3, 1998

(86) PCT No.: PCT/JP98/01571

§ 371 Date: Jan. 5, 2000

§ 102(e) Date: Jan. 5, 2000

(87) PCT Pub. No.: WO98/45249

PCT Pub. Date: Oct. 15, 1998

(30) Foreign Application Priority Data

Apr. 4, 1997 (JP) .................................................. 9-086255

(51) Int. Cl.[7] .................................................. A61H 31/22
(52) U.S. Cl. .......................... 514/546; 514/548; 514/630; 514/633; 564/221; 564/360; 560/194; 560/250; 560/252; 424/400
(58) Field of Search .................................... 514/546, 548, 514/630, 653; 564/221, 360; 560/144, 250, 252; 424/400

(56) References Cited

U.S. PATENT DOCUMENTS 3,660,488  5/1972  Cobb .

FOREIGN PATENT DOCUMENTS 0 627 406 A1   12/1994   (EP) .
0 778 263 A1    6/1997   (EP) .

OTHER PUBLICATIONS

B. Vithal Shetty and Allan R. Day, "Syntheses of Some 1–Alkylamino–1,1–di (hydroxymethyl)–2–phenylethanes", Nov. 1960, pp. 2057–2059.

*Primary Examiner*—Samuel Barts
(74) *Attorney, Agent, or Firm*—Evenson, McKeown, Edwards & Lenahan, P.L.L.C.

(57) ABSTRACT

The present invention relates to a compound of the general formula

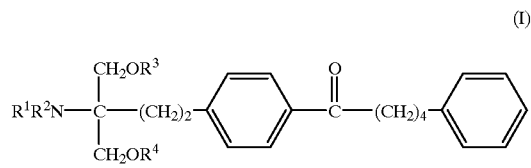

(I)

wherein $R^1$, $R^2$, $R^3$ and $R^4$ are each a hydrogen or an acyl, a pharmaceutically acceptable acid addition salt thereof or a hydrate thereof; a pharmaceutical comprising this compound; a pharmaceutical composition comprising this compound and a pharmaceutically acceptable carrier; and 2-amino-2-(2-(4-(1-hydroxy-5-phenylpentyl)phenyl)ethyl) propane-1,3-diol or 2-amino-2-(2-(4-formylphenyl)ethyl) propane-1,3-diol, the derivatives of the two compounds whose amino group and/or hydroxy group are(is) protected or a salt thereof. The compound of the present invention shows superior immunosuppressive action with less toxicity and higher safety, and is useful as a drug for prevention or suppression of rejection of organs or bone marrow transplantation, or as a drug for prevention or treatment of various autoimmune diseases or allergic diseases.

51 Claims, 1 Drawing Sheet

2-AMINOPROPANE-1,3-DIOL COMPOUNDS, MEDICINAL USE THEREOF, AND INTERMEDIATES IN SYNTHESIZING THE SAME

BACKGROUND OF THE INVENTION

The present invention relates to a 2-aminopropane-1,3-diol compound useful for pharmaceuticals, particularly immunosuppressants, a pharmaceutical use thereof and a synthetic intermediate therefor.

WO94/08943 discloses 2-aminopropane-1,3-diol compounds including 2-amino-2-(2-(4-octylphenyl)ethyl) propane-1,3-diol hydrochloride useful as a suppressant of rejection in organ or bone marrow transplantation, or as a therapeutic agent of various autoimmune diseases such as psoriasis, Behçet's disease and the like, and rheumatic diseases. WO96/06068 discloses a benzene compound useful as a suppressant of rejection in organ or bone marrow transplantation or as a therapeutic agent of various autoimmune diseases such as psoriasis, Behçet's disease and the like, and rheumatic diseases.

J. Org. Chem., vol. 25, p2057–2059 (1960) teaches 2-methylamino-2-(phenylmethyl or phenylmethyl substituted by 2-methyl, 3-methyl, 4-methyl, 4-methoxy or 4-hydroxy)propane-1,3-diol. In U.S. Pat. No. 3,660,488, 2amino-2-(p-chlorobenzyl)propane-1,3-diol as an antiradiation drug is disclosed.

The object of the present invention is to provide a more effective and highly safe compound as a suppressant of rejection in organ or bone marrow transplantation or as a therapeutic agent of autoimmune diseases such as atopic dermatitis, psoriasis, articular rheumatism and Behçet's disease, a pharmaceutical comprising the said compound, and a synthetic key compound of the said compound.

The present inventors have made intensive studies in order to achieve the above-mentioned object, and found that, of the 2-aminopropane-1,3-diol compounds represented by the general formula disclosed in WO94/08943

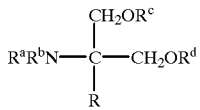

a compound wherein, at the substituent R of this compound, a p-phenylene group in the carbon chain and a phenyl group at the end of the carbon chain are substituted and, in the carbon chain between the said p-phenylene group and the phenyl group, the carbon at the β-position of the p-phenylene group is substituted by a carbonyl group (these compounds are not disclosed concretely in the said official gazette) possesses less toxicity, high safety and superior immunosuppressive action, which resulted in the completion of the present invention.

SUMMARY OF THE INVENTION

Namely, the present invention relates to the following.

(1) A 2-aminopropane-1,3-diol compound of the general formula (hereinafter sometimes to be referred to as Compound (I))

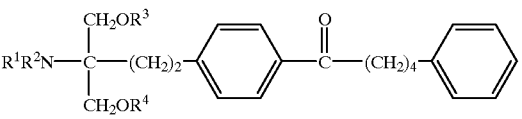

wherein $R^1$, $R^2$, $R^3$ and $R^4$ are the same or different and each is a hydrogen or an acyl; a pharmaceutically acceptable acid addition salt thereof or a hydrate thereof, (2) the 2-aminopropane-1,3-diol compound according to aforementioned (1), which is 2-amino-2-(2-(4-(1-oxo-5-phenylpentyl)phenyl)ethyl)propane-1,3diol (hereinafter sometimes to be referred to as Compound (I-a)), a pharmaceutically acceptable acid addition salt thereof or a hydrate thereof, (3) a pharmaceutical comprising the 2-aminopropane-1,3-diol compound according to the aforementioned (1) or (2), a pharmaceutically acceptable acid addition salt thereof or a hydrate thereof, (4) an immunosuppressant comprising, as an active ingredient, the 2aminopropane-1,3-diol compound according to the aforementioned (1) or (2), a pharmaceutically acceptable acid addition salt thereof or a hydrate thereof, (5) a suppressant of rejection comprising, as an active ingredient, the 2aminopropane-1,3-diol compound according to the aforementioned (1) or (2), a pharmaceutically acceptable acid addition salt thereof or a hydrate thereof, (6) an agent for the prevention or treatment of graft-versus-host diseases comprising, as an active ingredient, the 2-aminopropane-1,3-diol compound according to the aforementioned (1) or (2), a pharmaceutically acceptable acid addition salt thereof or a hydrate thereof, (7) an agent for the prevention or treatment of autoimmune diseases or allergic diseases comprising, as an active ingredient, the 2-aminopropane-1,3-diol compound according to the aforementioned (1) or (2), a pharmaceutically acceptable acid addition salt thereof or a hydrate thereof, (8) a pharmaceutical composition comprising the 2-aminopropane-1,3-diol compound according to the aforementioned (1) or (2), a pharmaceutically acceptable acid addition salt thereof or a hydrate thereof and a pharmaceutically acceptable carrier, (9) 2-amino-2-(2-(4-(1-hydroxy-5-phenylpentyl)phenyl) ethyl)propane-1,3-diol (hereinafter sometimes to be referred to as Compound (II)), a compound thereof wherein amino group and/or hydroxy group are(is) protected or a salt thereof,

(10) 2-amino-2-(2-(4-formylphenyl)ethyl)propane-1,3-diol (hereinafter sometimes to be referred to as Compound A), a compound thereof wherein amino group and/or hydroxy group are(is) protected or a salt thereof The compound of the present invention (I) is represented by the formula

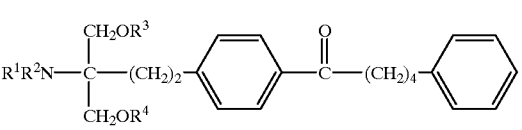

wherein each symbol is as defined above, and has structural characteristic that, in the carbon chain at the 2-position of the 2-aminopropane-1,3-diol skeleton, a p-phenylene group in the said carbon chain and a phenyl group at the end of the said carbon chain are substituted and, in the carbon chain between the said p-phenylene group and the phenyl group, the carbon at the α-position of the p-phenylene group is substituted by a carbonyl group. Due to this structural characteristic, the compound of the present invention possesses less toxicity and high safety and shows superior immunosuppressive action.

Compound (II) of the present invention is represented by the formula

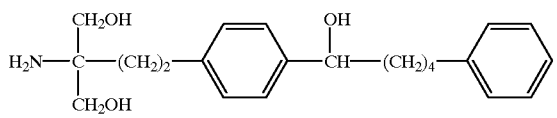

and Compound A of the present invention is represented by the formula

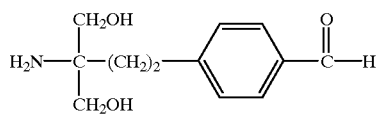

The groups represented by the respective symbols in the present specification are explained in the following.

The acyl at $R^1$, $R^2$, $R^3$ and $R^4$ is exemplified by a straight or branched chain alkanoyl having 1 to 6 carbon atoms such as formyl, acetyl, propionyl, butyryl, isobutyryl, pentanoyl and hexanoyl; a straight or branched chain alkanoyl having 2 to 6 carbon atoms which is substituted by phenyl, such as phenylacetyl and phenylpropionyl; an aroyl such as benzoyl; an alkoxycarbonyl wherein the alkoxy moiety is a straight or branched chain alkoxy having 1 to 6 carbon atoms, such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, tert-pentyloxycarbonyl and hexyloxycarbonyl; and an aralkyloxycarbonyl such as benzyloxycarbonyl.

Examples of the pharmaceutically acceptable acid addition salts of the present compound (I) include salts with an inorganic acid such as hydrochloric acid, hydrobromic acid, hydroiodic acid, sulfuric acid, nitric acid and phosphoric acid, or salts with an organic acid such as acetic acid, maleic acid, fumaric acid, benzoic acid, citric acid, succinic acid, tartaric acid, malic acid, mandelic acid, methanesulfonic acid, benzenesulfonic acid, p-toluenesulfonic acid and 10-camphorsulfonic acid. The present compound can be converted to salts thereof with oxalic acid to obtain crystals. The salts of compound (II) and compound A also include the aforementioned acid addition salts.

Examples of the hydrate of the present compound (I) include monohydrate, ½ hydrate, ⅕ hydrate, 2 hydrate and ³⁄₂ hydrate. The present invention also encompasses solvates.

The amino-protecting group of the compound (II) and compound A useful as a synthetic intermediate for the compound of the present invention is exemplified by an aliphatic acyl such as formyl, acetyl, propionyl, chloroacetyl, dichloroacetyl, trichloroacetyl, trifluoroacetyl, methanesulfonyl and ethanesulfonyl; an aromatic acyl such as phthaloyl, benzoyl, p-nitrobenzoyl, p-tert-butylbenzoyl, p-tert-butylbenzenesulfonyl, benzenesulfonyl and toluenesulfonyl; a carbonate such as methoxycarbonyl, ethoxycarbonyl, isopropoxycarbonyl, tert-butoxycarbonyl, 2-cyanoethoxycarbony, 2,2,2-trichloroethoxycarbonyl, benzyloxycarbonyl, p-nitrobenzyloxycarbonyl, p-methoxybenzyloxycarbonyl, p-chlorobenzyloxycarbonyl, diphenylmethoxycarbonyl, methoxymethyloxycarbonyl, acetylmethyloxycarbonyl, phenyloxycarbonyl, methylsulfonylethyloxycarbonyl and 2-trimethylsilylethoxycarbonyl; an amino-protecting group other than acyl such as trityl, di- or trialkylsilyl, benzyl and p-nitrobenzyl.

The hydroxyl-protecting group of compound (II) and compound A useful as a synthetic intermediate for the compound of the present invention is exemplified by a lower alkyl, which may be substituted, such as methyl, ethyl, propyl, butyl, tert-butyl, pentyl, hexyl, methoxymethyl and methoxyethoxymethyl; an allyl; an aralkyl, which may be substituted, such as benzyl, p-methoxybenzyl, triphenylmethyl and tris(p-methoxyphenyl)methyl; a tri-substituted silyl such as trimethylsilyl, triethylsilyl, tert-butyldimethylsilyl, tri-tert-butylsilyl, methyldiphenylsilyl, ethyldiphenylsilyl, propyldiphenylsilyl and tert-butyldiphenylsilyl; tetrahydropyranyl, tetrahydro-2-thiopyranyl, 2-thiolanyl; acyl such as an aliphatic acyl, an aromatic acyl and an aliphatic acyl substituted by an aromatic group, which are derived from carboxylic acids and sulfonic acids.

The aliphatic acyl is exemplified by a lower alkanoyl such as formyl, acetyl, propionyl, butyryl, valeryl, pivaloyl, carboxyacetyl, carboxypropionyl, trifluoroacetyl, chloroacetyl, methoxyacetyl and phenoxyacetyl; a carbonate such as methoxycarbonyl, ethoxycarbonyl, isopropoxycarbonyl, tert-butoxycarbonyl, 2,2,2-trichloroethoxycarbonyl, 2,2,2-tribromoethoxycarbonyl and p-nitrophenoxycarbonyl; a sulfonyl such as methanesulfonyl and ethanesulfonyl.

The aromatic acyl is exemplified by an aroyl such as benzoyl, toluoyl, naphthoyl, nitrobenzoyl and dinitrobenzoyl; a sulfonyl such as benzenesulfonyl, toluenesulfonyl, naphthalenesulfonyl, fluorobenzenesulfonyl, chlorobenzenesulfonyl, bromobenzenesulfonyl and iodobenzenesulfonyl; and the like. The aliphatic acyl substituted by an aromatic group is exemplified by an arylalkanoyl such as phenylacetyl, phenylpropionyl and phenylbutyryl.

Further, the two hydroxyl groups may in combination form a cyclic acetal such as methylene acetal, ethylidene acetal, isopropylidene acetal, benzylidene acetal, anisylidene acetal and 2,4-dimethoxybenzylidene acetal. Oxazolidine and oxazine may be formed together with the hydroxyl group and the amino group.

In the present invention, an amino group and/or a hydroxyl group of compound (I) may be protected by these protecting groups, and the protected compound can be used as a synthetic intermediate for compound (I), and occasionally, used as a pharmaceutical by itself The compound (I) of the present invention can be produced by the following methods.

Method A

Compound (I-a) wherein $R^1$, $R^2$, $R^3$ and $R^4$ are hydrogen in Compound (I) is produced by the following method. Namely, Compound A wherein an amino group and/or a hydroxyl group are/is protected, is reacted with a compound of the formula (III) [hereinafter referred to as Compound (III)]

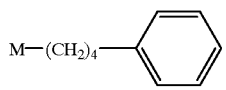

(III)

wherein M is a metal widely employed in the field of organic synthetic chemistry, such as lithium, magnesium chloride, magnesium bromide, magnesium iodide, copper, lithium copper and nickel; and a protecting group is removed, if necessary, to give Compound (II)

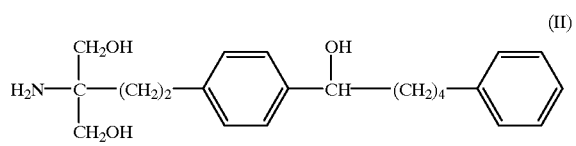

(II)

or a compound thereof wherein an amino group and/or a hydroxyl group are/is protected; followed by oxidation of the hydroxyl group at the α-position of the phenylene group with a suitable oxidizing agent, and a protecting group is removed, if necessary, to give Compound (I-a).

Examples of the organic solvent to be used in the reaction with Compound (III) include tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The reaction temperature of the present reaction is generally from −100 to 80° C. and a lower or higher temperature than the said temperature range may be selected on demand.

The reaction time of the present reaction is generally from 30 minutes to 2 days and a longer or shorter reaction period than the indicated period may be selected on demand.

After the reaction is carried out under the above-mentioned conditions or after removing the protecting group(s) on demand, Compound (II) can be purified by a method known in the field of organic synthetic chemistry, such as solvent extraction, recrystallization, chromatography or a method using an ion exchange resin.

Examples of the oxidizing agent to be used in the oxidation reaction of Compound (II) include chromic acid-sulfuric acid, chromium oxide(VI)sulfuric acid-acetone (Jones reagent), chromiun oxide (VI)-pyridine complex (Collins reagent), dichromate (e.g. sodium dichromate, potassium dichromate)-sulfuric acid, pyridinium chlorochromate (PPC), manganese dioxide, dimethysulfoxide-electrophilic activated reagent (dicyclohexylcarbodiimide, acetic anhydride, (di)phosphorous pentaoxide, sulfur trioxide-pyridine complex, trifluoroacetic anhydride, oxalyl chloride, halogen), sodium hypochlorite, potassium hypochlorite, sodium bromite, N-bromosuccinimide, N-chlorosuccinimide, N-bromoacetamide, 2,3-dichloro-5,6-dicyano-p-benzoquinone, tetrachloro-p-benzoquinone, tetrachloro-o-benzoquinone, nitric acid, dinitrogen tetraoxide, anhydrous benzeneseleninic acid, ruthenium tetraoxide, ruthenium dioxide-sodium periodate, bischlorobis(triphenylphosphine)ruthenium-iodosylbenzene or sodium bismuthate.

Examples of the solvent to be used in the present reaction include water, acetic acid, diethyl ether, tetrahydrofuran, dioxane, acetone, tert-butyl alcohol, methylene chloride, chloroform, hexane, benzene, toluene or a mixture thereof.

The reaction temperature of the present reaction is generally from 0 to 100° C. and a lower or higher temperature than the said temperature range may be selected on demand.

The reaction time of the present reaction is generally from 30 minutes to 2 days and a longer or shorter reaction period than the indicated period may be selected on demand.

After the reaction is carried out under the above-mentioned conditions or after removing the protecting group(s) on demand, Compound (I-a) can be purified by a method known in the field of organic synthetic chemistry, such as solvent extraction, recrystallization, chromatography or a method using an ion exchange resin.

Method B

Compound (I), wherein $R^1$, $R^2$, $R^3$ and $R^4$ are acyl, is produced by the following method. Namely, Compound (I-a) is protected on demand and reacted with acyl halide in the presence of a base, followed by removal of the protecting group(s) on demand to give the compound wherein the corresponding amino group and/or hydroxyl group are/is acylated. In the present method, Compound (II) instead of Compound (I-a) is reacted and treated in the same manner to allow production of the Compound (II) wherein an amino group and/or a hydroxyl group are/is acylated. Compound (I), wherein $R^1$, $R^{2,}$ $R^3$ and $R^4$ are acyl, is treated with an acid or a base to produce Compound (I-a).

Compound A useful as an synthetic intermediate for Compound (I) of the present invention can be produced by the following method.

Method C

A compound of the general formula (IV) [hereinafter referred to as Compound (IV)]

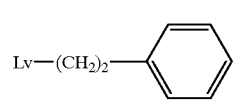

(IV)

wherein Lv is a leaving group widely employed in the field of organic synthetic chemistry, such as halogen (fluorine, chlorine, bromine, iodine), methanesulfonyloxy, p-toluenesulfonyloxy and trifluoromethanesulfoyloxy, and a compound of the general formula (V) [hereinafter referred to as Compound (V)]

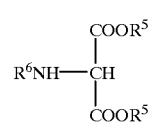

(V)

wherein $R^5$ is a lower alkyl such as methyl, ethyl, propyl, isopropyl, butyl and tert-butyl, or aralkyl such as benzyl, nitrobenzyl, methoxybenzyl and methylbenzyl, $R^6$ is an amino-protecting group widely employed in the field of organic synthetic chemistry, such as acetyl, benzoyl, tert-butoxycarbonyl and benzyloxycarbonyl, and the two $R^5$s in the molecule may in combination form a ring such as dioxane and $R^5$ and $R^6$ in the molecule may in combination form a ring such as oxazolidine and oxazine, are condensed in the presence of a base to give a compound of the general formula (VI) [hereinafter referred to as Compound (VI)]

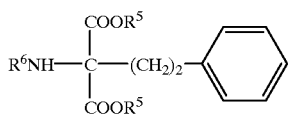

(VI)

wherein R⁵ and R⁶ are as defined above; the ester groups are reduced with a suitable reducing agent and protecting group (s) is/are introduced or removed on demand to give a compound of the general formula (VII) [hereinafter referred to as Compound (VII)]

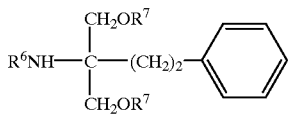

(VII)

wherein $R^7$ is a hydroxyl-protecting group widely employed in the field of organic synthetic chemistry such as acetyl, benzoyl, benzyl, trimethylsilyl, tert-butyldimethylsilyl, methoxymethyl, methoxyethoxymethyl and tetrahydropyranyl, and $R^6$ is as defined above; the obtained compound is subjected to reaction with dichloromethyl methyl ether in the presence of a Lewis acid, and protecting group(s) may be introduced or removed as necessary to give Compound A or N- and/or O-protected compound thereof.

Examples of the base to be used in the condensation include sodium hydroxide, sodium methoxide, sodium ethoxide, sodium hydride, potassium hydride, lithium diisopropylamide, butyllithium, lithium hexamethyldisilazane, triethylamine, diisopropylethylamine and 1,8diazabicyclo[5.4.0]undec-7-ene.

Examples of the organic solvent to be used in the condensation include methanol, ethanol, tert-butyl alcohol, tertrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The reaction temperature of the condensation is generally from −20 to 150° C. and a lower or higher temperature than the said temperature range may be selected on demand.

The reaction time of the condensation is generally from 30 minutes to 2 days and a longer or shorter reaction period than the indicated period may be selected on demand.

After the condensation is carried out under the above-mentioned conditions or after removing the protecting group (s) on demand, Compound (VI) can be purified by a method known in the field of organic synthetic chemistry, such as solvent extraction, recrystallization, chromatography or a method using an ion exchange resin.

Examples of the reducing agent to be used in the reduction of ester include, for example, a metal reducing reagent such as sodium borohydride, lithium borohydride or lithium aluminum hydride, or diborane.

Examples of the solvent to be used in the reduction of ester include, for example, water, methanol, ethanol, 1-propanol, 2-propanol, tert-butyl alcohol, tetrahydrofuran, dioxane, diethyl ether, ethylene glycol dimethyl ether or a mixture thereof.

The reaction temperature of the reduction of ester is generally from −20 to 80° C. and a lower or higher temperature than the said temperature range may be selected on demand.

The reaction time of the reduction of ester is generally from 30 minutes to 10 hours and a longer or shorter reaction period than the indicated period may be selected on demand.

After the reduction is carried out under the above-mentioned conditions or after removing the protecting group (s) on demand, the objective compound can be purified by a method known in the field of organic synthetic chemistry, such as solvent extraction, recrystallization, chromatography or a method using an ion exchange resin.

Examples of the Lewis acid to be used in the reaction with dichloromethyl methyl ether include aluminum chloride, titanium tetrachloride, tin tetrachloride, antimony(V) chloride, iron(III) chloride, boron trifluoride, bismuth(III) chloride, zinc chloride and mercury(II) chloride.

Examples of the organic solvent to be used in the reaction with dichloromethyl methyl ether include tetrahydrofuran, diethyl ether, ethylene glycol dimethyl ether, dimethylformamide, dimethyl sulfoxide, methylene chloride, chloroform, dichloroethane, acetonitrile, nitromethane and carbon disulfide. The reaction may be carried out without solvent where necessary.

The temperature of the reaction with dichloromethyl methyl ether is generally from −20 to 0° C. and a lower or higher temperature than the said temperature range may be selected on demand.

The time of the reaction with dichloromethyl methyl ether is generally from 30 minutes to 24 hours and a longer or shorter reaction time than the indicated period may be selected on demand.

After the reaction with dichloromethyl methyl ether is carried out under the above-mentioned conditions or after removing the protecting group on demand, the objective compound can be purified by a method known in the field of organic synthetic chemistry, such as solvent extraction, recrystallization, chromatography or a method using an ion exchange resin.

As other methods to synthesize Compound A from Compound (VII) include (1) a method comprising Vilsmeier reaction using N,N-dimethylformamide, N-methylformanilide, N-formylmorpholine or N,N-diisopropylformamide, and a halogenating reagent such as phosphoryl chloride, phosgene, oxalyl chloride, thionyl chloride, triphenylphosphine bromine or hexachlorotriphosphazatriene, and hydrolysis, (2) a method comprising reaction with hexamethylenetetramine in the presence of an acid catalyst (e.g., acetic acid, triphenylacetic acid) and hydrolysis (Duff method), (3) a method comprising reaction of a combination of carbon monoxide and hydrogen chloride, or a combination of formic acid and chlorosulfuric acid, thionyl chloride or phosphorus oxychloride in the presence of aluminum chloride using copper(I) chloride as a cocatalyst as necessary (Gattermann-Koch method), (4) a method comprising reaction of dry hydrogen cyanide and hydrochloric acid (Gattermann method) and the like.

Method D

Using, in Method C, a compound of the general formula (VIII) [hereinafter referred to as Compound (VIII)]

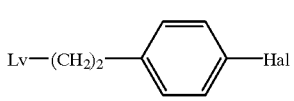

(VIII)

wherein Hal is halogen such as chlorine, bromine or iodine, Lv is as defined above, instead of Compound (IV), a compound of the general formula (IX) [hereinafter referred to as Compound (IX)]

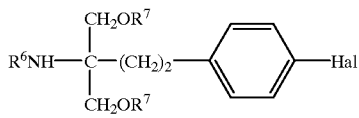
(IX)

wherein $R^6$, $R^7$ and Hal are as defined above, is obtained; the obtained compound is reacted with a formylating agent in the presence of magnesium and subjected to hydrolysis; and protecting group(s) is/are removed, if necessary, to give Compound A or N- and/or O-protected compound thereof.

Examples of the formylating agent to be used in the present reaction include formate such as methyl orthoformate, ethyl orthoformate, ethyl formate or lithium formate, or formamide such as N-methylformanilide, N,N-dimethylformamide, N-methyl-N-(2-pyridyl)formamide, 1formylpiperidine, 4-formylmorpholine or ethoxymethyleneaniline produced from ethyl orthoformate and aniline, fluoroformaldehyde (FCHO), formic anhydride ((HCO)$_2$O) and acetic formic anhydride (HCOOCOCH$_3$).

Examples of the organic solvent to be used in the present reaction include tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The reaction temperature of the present reaction is generally from –100 to 80° C. and a lower or higher temperature than the said temperature range may be selected on demand.

The reaction period of the present reaction is generally from 30 minutes to 2 days and a longer or shorter reaction period than the indicated period may be selected on demand.

After the reaction is carried out under the above-mentioned conditions or after removing the protecting group (s) on demand, Compound A can be purified by a method known in the field of organic synthetic chemistry, such as solvent extraction, recrystallization, chromatography or a method using an ion exchange resin.

Method E

A compound of the general formula (X) [hereinafter referred to as Compound (X)]

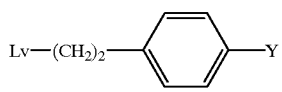
(X)

wherein Y is a formyl group or a protected formyl equivalent such as dimethoxymethyl, diethoxymethyl, ethylenedioxymethyl, propylenedioxymethyl, ethylenedithiomethyl or propylenedithiomethyl, Lv is as defined above; is subjected to condensation, in the presence of a base, with a compound of the general formula (XI) [hereinafter referred to as Compound (XI)]

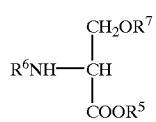
(XI)

wherein $R^5$, $R^6$ and $R^7$ are as defined above; to give a compound of the general formula (XII) [hereinafter referred to as Compound (XII)]

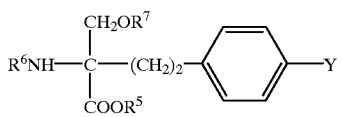
(XII)

wherein $R^5$, $R^6$, $R^7$ and Y are as defined above; the ester group is subjected to reduction with a suitable reducing agent and protecting group(s) is/are introduced or removed, if necessary, to give Compound A or N- and/or O-protected compound thereof.

Examples of the base to be used in the condensation include sodium hydroxide, sodium methoxide, sodium ethoxide, sodium hydride, potassium hydride, lithium diisopropylamide, butyllithium, lithium hexamethyldisilazane, triethylamine, diisopropylethylamine and 1,8diazabicyclo[5.4.0]undec-7-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The reaction temperature of the condensation is generally from –20 to 150° C. and a lower or higher temperature than the said temperature range may be selected on demand.

The reaction period of the condensation is generally from 30 minutes to 2 days and a longer or shorter reaction period than the indicated period may be selected on demand.

After the condensation is carried out under the above-mentioned conditions or after removing the protecting group (s) on demand, Compound (XII) can be purified by a method known in the field of organic synthetic chemistry, such as solvent extraction, recrystallization, chromatography or a method using an ion exchange resin.

Examples of the reducing agent to be used in the reduction of ester include metal reducing reagent such as sodium borohydride, lithium borohydride or lithium aluminum hydride, or diborane.

Examples of the solvent to be used in the reduction of ester include water, methanol, ethanol, 1-propanol, 2-propanol, tert-butyl alcohol, tetrahydrofuran, dioxane, diethyl ether, ethylene glycol dimethyl ether or a mixture thereof.

The reaction temperature of the reduction of ester is generally from –20 to 80° C. and a lower or higher temperature than the said temperature range may be selected on demand.

The reaction period of the reduction of ester is generally from 30 minutes to 10 hours and a longer or shorter reaction period than the indicated period may be selected on demand.

After the reduction is carried out under the above-mentioned conditions or after removing the protecting group (s) on demand, the objective compound can be purified by a method known in the field of organic synthetic chemistry, such as solvent extraction, recrystallization, chromatography or a method using an ion exchange resin.

Method F

A compound of the general formula (XIII) [hereinafter referred to as Compound (XIII)]

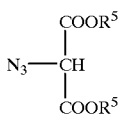

(XIII)

wherein $R^5$ is as defined above; is subjected to condensation, in the presence of a base, with Compound (X) to give a compound of the general formula (XIV) [hereinafter referred to as Compound]

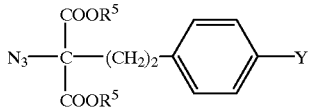

(XIV)

wherein $R^5$ and Y are as defined above; the ester groups and the azide group are subjected to reduction with a suitable reducing agent and protecting group(s) is/are introduced or removed, if necessary, to give Compound A or N- and/or O-protected compound thereof.

Examples of the base to be used in the condensation include sodium hydroxide, sodium methoxide, sodium ethoxide, sodium hydride, potassium hydride, lithium diisopropylamide, butyllithium, lithium hexamethyldisilazane, triethylamine, diisopropylethylamine and 1,8diazabicyclo[5.4.0]undec-7-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane or acetonitrile.

The reaction temperature of the condensation is generally from −20 to 150° C. and a lower or higher temperature than the said temperature range may be selected on demand.

The reaction period of the condensation is generally from 30 minutes to 2 days and a longer or shorter reaction period than the indicated period may be selected on demand.

After the condensation is carried out under the above-mentioned conditions or after removing the protecting group (s) on demand, Compound (XIV) can be purified by a method known in the field of organic synthetic chemistry, such as solvent extraction, recrystallization, chromatography or a method using an ion exchange resin.

Examples of the reducing agent to be used in the reduction of ester include metal reducing reagent such as sodium borohydride, lithium borohydride and lithium aluminum hydride, or diborane.

Examples of the solvent to be used in the reduction of ester include water, methanol, ethanol, 1-propanol, 2-propanol, tert-butyl alcohol, tetrahydrofuran, dioxane, diethyl ether, ethylene glycol dimethyl ether or a mixture thereof.

The reaction temperature of the reduction of ester is generally from −20 to 80° C. and a lower or higher temperature than the said temperature range may be selected on demand.

The reaction period of the reduction of ester is generally from 30 minutes to 10 hours and a longer or shorter reaction period than the indicated period may be selected on demand.

Examples of the reducing agent to be used in the reduction of azide include metal reducing reagent such as sodium borohydride, lithium borohydride and lithium aluminum hydride, and triphenylphosphine. Catalytic reduction using transition metal such as palladium-carbon, platinum oxide, Raney nickel, rhodium or ruthenium is also effective.

Examples of the solvent to be used in the reduction of azide include water, methanol, ethanol, 1-propanol, 2-propanol, tert-butyl alcohol, tetrahydrofuran, diethyl ether, dioxane, ethylene glycol dimethyl ether, acetone, ethyl acetate, acetic acid, benzene, toluene, xylene, dimethylformamide, dimethyl sulfoxide or a mixture thereof.

The reaction temperature of the reduction of azide is generally from −20 to 80° C. and a lower or higher temperature than the said temperature range may be selected on demand.

After the reduction is carried out under the above-mentioned conditions or after removing the protecting group (s) on demand, the objective compound can be purified by a method known in the field of organic synthetic chemistry, such as solvent extraction, recrystallization, chromatography or a method using an ion exchange resin.

Method G

A compound of the general formula (XV) [hereinafter to be referred to as Compound (XV)]

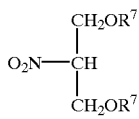

(XV)

wherein $R^7$ is a protecting group of a hydroxyl group widely employed in the field of organic synthetic chemistry, such as acetyl, benzoyl, benzyl, trimethylsilyl, tert-butyldimethylsilyl, methoxymethyl, methoxyethoxymethyl or tetrahydropyranyl, and the two $R^7$s may in combination form a ring such as dioxane; is subjected to condensation, in the presence of a base, with Compound (X) to give a compound of the general formula (XVI) [hereinafter referred to as Compound (XVI)]

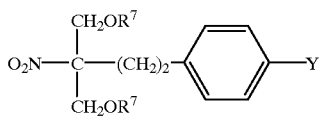

(XVI)

wherein $R^7$ and Y are as defined above; and the nitro group is subjected to reduction with a suitable reducing agent and protecting group(s) is/are introduced or removed, if necessary, to give Compound A or N- and/or O-protected compound thereof.

Examples of the base to be used in the condensation include sodium hydroxide, sodium methoxide, sodium ethoxide, sodium hydride, potassium hydride, lithium diisopropylamide, butyllithium, lithium hexamethyldisilazane, triethylamine, diisopropylethylamine and 1,8diazabicyclo[5.4.0]undec-7-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane or acetonitrile.

The reaction temperature of the condensation is generally from −20 to 150° C. and a lower or higher temperature than the said temperature range may be selected on demand.

The reaction period of the condensation is generally from 30 minutes to 2 days and a longer or shorter reaction period than the indicated period may be selected on demand.

After the condensation is carried out under the above-mentioned conditions or after removing the protecting group(s) on demand, Compound (XVI) can be purified by a method known in the field of organic synthetic chemistry, such as solvent extraction, recrystallization, chromatography or a method using an ion exchange resin.

Examples of the reducing agent to be used in the reduction of nitro include a metal reducing reagent such as sodium borohydride, lithium borohydride or lithium aluminum hydride, transition metal such as palladium-carbon, platinum oxide, Raney nickel, rhodium or rutenium for catalytic reduction, a metal such as iron, zinc or tin.

Examples of the solvent to be used in the reduction of nitro include water, methanol, ethanol, tert-butyl alcohol, tetrahydrofuran, diethyl ether, dioxane, acetone, ethyl acetate, acetic acid, benzene, toluene, xylene, dimethylformamide, dimethyl sulfoxide or a mixture thereof.

The reaction temperature of the reduction of nitro is generally from −20 to 80° C. and a lower or higher temperature than the said temperature range may be selected on demand.

After the reduction is carried out under the above-mentioned conditions or after removing the protecting group(s) on demand, the objective compound can be purified by a method known in the field of organic synthetic chemistry, such as solvent extraction, recrystallization, chromatography or a method using an ion exchange resin.

Method H

A compound of the general formula (XVII) [hereinafter referred to as Compound (XVII)]

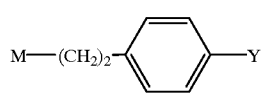

(XVII)

wherein M and Y are as defined above; is subjected to nucleophilic addition with a compound of the general formula (XVIII) [hereinafter to be referred to as Compound (XVIII)]

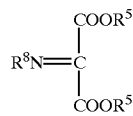

(XVIII)

wherein $R^8$ is an imino-protecting group widely employed in the field of organic synthetic chemistry, such as acetyl, benzoyl or tert-butoxycarbonyl, benzyloxycarbonyl, and $R^5$ is as defined above; to give a compound of the general formula (VI-a) [hereinafter referred to as Compound (VI-a)]

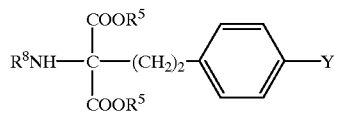

(VI-a)

wherein $R^5$, $R^8$ and Y are as defined above; the ester groups are subjected to reduction with a suitable reducing agent and protecting group(s) is/are introduced or removed, if necessary, to give Compound A or N- and/or O-protected compound thereof.

Examples of the organic solvent to be used in the addition include tetrahydrofuran, diethyl ether, ethylene glycol dimethyl ether, dimethylformamide, dimethyl sulfoxide, benzene, toluene, xylene, dioxane, methylene chloride, chloroform, dichloroethane or acetonitrile.

The reaction temperature of the addition is generally from −100 to 80° C. and a lower or higher temperature than the said temperature range may be selected on demand.

The reaction period of the addition is generally from 30 minutes to 2 days and a longer or shorter reaction period than the indicated period may be selected on demand.

After the addition is carried out under the above-mentioned conditions or after removing the protecting group(s) on demand, Compound (VI-a) can be purified by a method known in the field of organic synthetic chemistry, such as solvent extraction, recrystallization, chromatography or a method using an ion exchange resin.

Examples of the reducing agent to be used in the reduction of ester include a metal reducing reagent such as sodium borohydride, lithium borohydride or lithium aluminum hydride, or diborane.

Examples of the solvent to be used in the reduction of ester include water, methanol, ethanol, 1-propanol, 2-propanol, tert-butyl alcohol, tetrahydrofuran, dioxane, diethyl ether, ethylene glycol dimethyl ether or a mixture thereof.

The reaction temperature of the reduction of ester is generally from −20 to 80° C. and a lower or higher temperature than the said temperature range may be selected on demand.

The reaction period of the reduction of ester is generally from 30 minutes to 10 hours and a longer or shorter reaction period than the indicated period may be selected on demand.

After the reduction is carried out under the above-mentioned conditions or after removing the protecting group(s) on demand, the objective compound can be purified by a method known in the field of organic synthetic chemistry, such as solvent extraction, recrystallization, chromatography or a method using an ion exchange resin.

Method I

Compound (XVI) can be also produced by the following method.

Compound (X) and a compound of the general formula (XIX) [hereinafter referred to as Compound (XIX)]

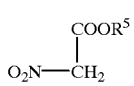

(XIX)

wherein $R^5$ is as defined above; are subjected to condensation in the presence of a base to give a compound of the general formula (XX) [hereinafter referred to as Compound (XX)]

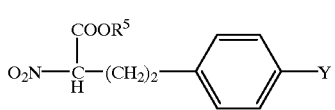

(XX)

wherein $R^5$ and Y are as defined above; the obtained compound is subjected to condensation, in the presence of a base, with formalin and protection of hydroxyl group if necessary to give a compound of the general formula (XXI) [hereinafter referred to as Compound (XXI)]

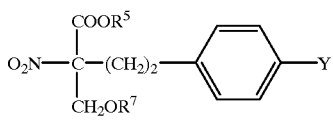
(XXI)

wherein $R^5$, $R^7$ and Y are as defined above; the ester group is subjected to reduction with a suitable reducing agent and protection of the hydroxyl group(s) if necessary to give Compound (XVI).

Examples of the solvent to be used in the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane or acetonitrile.

Examples of the base to be used in the condensation include sodium hydroxide, sodium methoxide, sodium ethoxide, sodium hydride, potassium hydride, triethylamine, diisopropylethylamine and 1,8diazabicyclo[5.4.0]undec-7-ene.

The reaction temperature of the condensation is generally from −20 to 150° C. and a lower or higher temperature than the said temperature range may be selected on demand.

The reaction period of the condensation is generally from 30 minutes to 2 days and a longer or shorter reaction period than the indicated period may be selected on demand.

After the condensation is carried out under the above-mentioned conditions or after removing the protecting group (s) on demand, Compound (XX) can be purified by a method known in the field of organic synthetic chemistry, such as solvent extraction, recrystallization, chromatography or a method using an ion exchange resin.

Examples of the solvent to be used in the condensation with formalin include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform or acetonitrile.

Examples of the base to be used in the condensation include sodium hydroxide, sodium methoxide, sodium ethoxide, sodium hydride, potassium hydride, triethylamine, diisopropylethylamine and 1,8diazabicyclo[5.4.0]undec-7-ene.

The reaction temperature of the condensation is generally from −20 to 150° C. and a lower or higher temperature than the said temperature range may be selected on demand.

The reaction period of the condensation is generally from 30 minutes to 2 days and a longer or shorter reaction period than the indicated period may be selected on demand.

After the condensation is carried out under the above-mentioned conditions or after removing the protecting group (s) on demand, Compound (XXI) can be purified by a method known in the field of organic synthetic chemistry, such as solvent extraction, recrystallization, chromatography or a method using an ion exchange resin.

Examples of the reducing agent to be used in the reduction of ester include a metal reducing reagent such as sodium borohydride, lithium borohydride or lithium aluminum hydride, or diborane.

Examples of the solvent to be used in the reduction of ester include water, methanol, ethanol, 1-propanol, 2-propanol, tert-butyl alcohol, tetrahydrofuran, dioxane, diethyl ether, ethylene glycol dimethyl ether or a mixture thereof.

The reaction temperature of the reduction of ester is generally from −20 to 80° C. and a lower or higher temperature than the said temperature range may be selected on demand.

The reaction period of the reduction of ester is generally from 30 minutes to 10 hours and a longer or shorter reaction period than the indicated period may be selected on demand.

After the reduction is carried out under the above-mentioned conditions or after removing the protecting group (s) on demand, Compound (XVI) can be purified by a method known in the field of organic synthetic chemistry, such as solvent extraction, recrystallization, chromatography or a method using an ion exchange resin.

Method J

Compound (VI-a) can be also produced in the following method.

A compound of the general formula (XXII) [hereinafter referred to as Compound (XXII)]

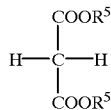
(XXII)

wherein $R^5$ is as defined above; and Compound (X) are subjected to condensation in the presence of a base to give a compound of the general formula (XXIII) [hereinafter referred to as Compound (XXIII)]

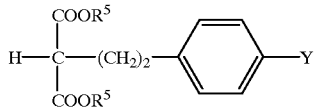
(XXIII)

wherein $R^5$ and Y are as defined above; the obtained compound is reacted, in the presence of a base, with an amination agent of the general formula (XXIV)

$$H_2N-Le \qquad (XXIV)$$

wherein Le is a leaving group such as 2,4-dinitrophenoxy; and protecting group(s) is/are introduced or removed if necessary to give Compound (VI-a).

Examples of the base to be used in the condensation include sodium hydroxide, sodium methoxide, sodium ethoxide, sodium hydride, potassium hydride, lithium diisopropylamide, butyllithium, lithium hexamethyldisilazane, triethylamine, diisopropylethylamine and 1,8diazabicyclo[5.4.0]undec-7-ene.

Examples of the solvent to be used in the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane or acetonitrile.

The reaction temperature of the condensation is generally from −20 to 150° C. and a lower or higher temperature than the said temperature range may be selected on demand.

The reaction period of the condensation is generally from 30 minutes to 2 days and a longer or shorter reaction period than the indicated period may be selected on demand.

After the condensation is carried out under the above-mentioned conditions or after removing the protecting group(s) on demand, Compound (XXIII) can be purified by a method known in the field of organic synthetic chemistry, such as solvent extraction, recrystallization, chromatography or a method using an ion exchange resin.

Examples of the base to be used in the amination reaction include sodium hydroxide, sodium methoxide, sodium ethoxide, sodium hydride, potassium hydride, lithium diisopropylamide, butyllithium, lithium hexamethyldisilazane, triethylamine, diisopropylethylamine and 1,8-diazabicyclo[5.4.0]undec-7-ene.

Examples of the solvent to be used in the amination reaction include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane or acetonitrile.

The reaction temperature of the amination reaction is generally from −20 to 150° C. and a lower or higher temperature than the said temperature range may be selected on demand.

The reaction period of the amination reaction is generally from 30 minutes to 2 days and a longer or shorter reaction period than the indicated period may be selected on demand.

After the amination reaction is carried out under the above-mentioned conditions or after removing the protecting group(s) on demand, Compound (VI-a) can be purified by a method known in the field of organic synthetic chemistry, such as solvent extraction, recrystallization, chromatography or a method using an ion exchange resin.

Method K

In Method E to Method J, Compound (IV) or Compound (VIII) is used instead of Compound (X) to give Compound (VII) or Compound (IX), respectively.

Method L

In Method C, Compound (X) is used instead of Compound (IV) to give Compound (VI-a).

The compound (I-a) of the present invention can be also produced by the following method.

Method M

A compound of the general formula (XXV) [hereinafter referred to as Compound (XXV)]

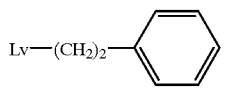

(XXV)

wherein Lv is as defined above; is reacted with dichloromethyl methyl ether in the presence of a Lewis acid to give a compound of the general formula (XXVI) [hereinafter referred to as Compound (XXVI)]

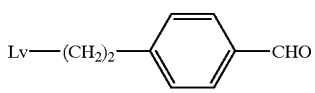

(XXVI)

wherein Lv is as defined above; the obtained compound is reacted with Compound (III) to give a compound of the general formula (XXVII) [hereinafter referred to as Compound (XXVII)]

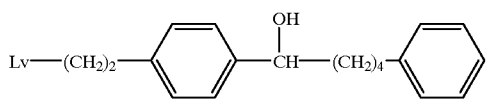

(XXVII)

wherein Lv is as defined above; the obtained compound is subjected to oxidation with a suitable oxidizing agent to give a compound of the general formula (XXVIII) [hereinafter referred to as Compound (XXVIII)]

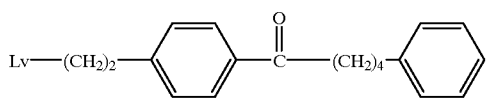

(XXVIII)

wherein Lv is as defined above; the obtained compound is subjected to condensation with Compound (V) in the presence of a base to give a compound of the general formula (XXIX) [hereinafter referred to as Compound (XXIX)]

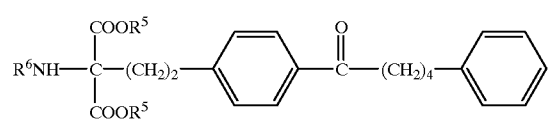

(XXIX)

wherein $R^5$ and $R^6$ are as defined above; the carbonyl group of Compound (XXIX) is subjected to protection and reduction with a reducing agent to give a compound of the general formula (I-b) [hereinafter referred to as Compound (I-b)]

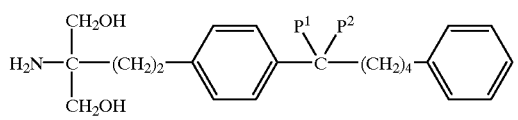

(I-b)

wherein $P^1$ and $P^2$ are carbonyl-protecting group widely employed in the field of organic synthetic chemistry, such as a lower alkoxy such as methoxy, ethoxy, propoxy, isopropoxy or butoxy, or $P^1$ and $P^2$ together form an alkylenedioxy such as ethylenedioxy, or a compound thereof wherein the amino group and/or the hydroxyl group are(is) protected; and the obtained compound is subjected to deprotection to give Compound (I-a).

Examples of the Lewis acid to be used in the reaction with dichloromethyl methyl ether include aluminum chloride, titanium tetrachloride, tin tetrachloride, antimony(V) chloride, iron(III) chloride, boron trifluoride, bismuth(III) chloride, zinc chloride or mercury(II) chloride.

Examples of the organic solvent to be used in the reaction with dichloromethyl methyl ether include tetrahydrofuran, diethyl ether, ethylene glycol dimethyl ether, dimethylformamide, dimethyl sulfoxide, methylene chloride, chloroform, dichloroethane, acetonitrile, nitromethane or carbon disulfide. The reaction may be carried out without solvent on demand.

The reaction temperature of the reaction with dichloromethyl methyl ether is generally from −20 to 0° C. and a lower or higher temperature than the said temperature range may be selected on demand.

The reaction period of the reaction with dichloromethyl methyl ether is generally from 30 minutes to 24 hours and a longer or shorter reaction period than the indicated period may be selected on demand.

After the reaction with dichloromethyl methyl ether is carried out under the above-mentioned conditions or after removing the protecting group(s) on demand, the objective compound can be purified by a method known in the field of organic synthetic chemistry, such as solvent extraction, recrystallization, chromatography or a method using an ion exchange resin.

Examples of the organic solvent to be used in the reaction with Compound (III) include tetrahydrofuran, diethyl ether, ethylene glycol dimethyl ether, dimethylformamide, dimethyl sulfoxide, benzene, toluene, xylene, dioxane, methylene chloride, chloroform, dichloroethane or acetonitrile.

The reaction temperature of the present reaction is generally from -100 to 80° C. and a lower or higher temperature than the said temperature range may be selected on demand.

The reaction period of the present reaction is generally from 30 minutes to 2 days and a longer or shorter reaction period than the indicated period may be selected on demand.

After the reaction is carried out under the above-mentioned conditions or after removing the protecting group(s) on demand, Compound (XXVII) can be purified by a method known in the field of organic synthetic chemistry, such as solvent extraction, recrystallization, chromatography or a method using an ion exchange resin.

Examples of the oxidizing agent to be used in the oxidation of Compound (XXVII) include chromic acid-sulfuric acid, chromium(VI) oxide-sulfuric acid-acetone (Jones reagent), chromium(VI) oxide-pyridine complex (Collins reagent), dichromate (sodium dichromate, potassium dichromate, etc.)-sulfuric acid, pyridinium chlorochromate (PCC), manganese dioxide, dimethyl sulfoxide-electrophilic activated reagent (dicyclohexylcarbodiimide, acetic anhydride, phosphorus pentaoxide, sulfur trioxide-pyridine complex, trifluoroacetic anhydride, oxalyl chloride, halogen), sodium hypochlorite, potassium hypochlorite, sodium bromite, N-bromosuccinimide, N-chlorosuccinimide, N-bromoacetamide, 2,3-dichloro-5,6-dicyano-p-benzoquinone, tetrachloro-p-benzoquinone, tetrachloro-o-benzoquinone, nitric acid, dinitrogen tetraoxide, anhydrous benzeneseleninic acid, ruthenium tetraoxide, rutenium dioxide-sodium periodate, bischlorobis (triphenylphosphine)rutenium-iodosylbenzene or sodium bismuthate.

Examples of the solvent to be used in the present reaction include water, acetic acid, diethyl ether, tetrahydrofuran, dioxane, acetone, tert-butyl alcohol, methylene chloride, chloroform, hexane, benzene, toluene or a mixture thereof.

The reaction temperature of the present reaction is generally from 0 to 100° C. and a lower or higher temperature than the said temperature range may be selected on demand.

The reaction period of the present reaction is generally from 30 minutes to 2 days and a longer or shorter reaction period than the indicated period may be selected on demand.

After the reaction is carried out under the above-mentioned conditions or after removing the protecting group(s) on demand, Compound (XXVIII) can be purified by a method known in the field of organic synthetic chemistry, such as solvent extraction, recrystallization, chromatography or a method using an ion exchange resin.

Examples of the base to be used in the condensation include sodium hydroxide, sodium methoxide, sodium ethoxide, sodium hydride, potassium hydride, lithium diisopropylamide, butyllithium, lithium hexamethyldisilazane, triethylamine, diisopropylethylamine and 1,8diazabicyclo[5.4.0]undec-7-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane or acetonitrile.

The reaction temperature of the condensation is generally from −20 to 150° C. and a lower or higher temperature than the said temperature range may be selected on demand.

The reaction period of the condensation is generally from 30 minutes to 2 days and a longer or shorter reaction period than the indicated period may be selected on demand.

After the condensation is carried out under the above-mentioned conditions or after removing the protecting group(s) on demand, Compound (XXIX) can be purified by a method known in the field of organic synthetic chemistry, such as solvent extraction, recrystallization, chromatography or a method using an ion exchange resin.

Compound (XXVIII) wherein Lv is halogen, particularly chlorine or bromine, is also subjected to iodination using sodium iodide, followed by reacting with Compound (V).

The protection of the carbonyl group of Compound (XXIX) can be carried out by a method known in the field of organic synthetic chemistry. For example, Compound (XXIX) is treated with ethylene glycol in the presence of an acid catalyst such as paratoluenesulfonic acid, or with lower alcohol in the presence of an acid such as hydrochloric acid or sulfuric acid to give the corresponding carbonyl-protected compound.

Examples of the reducing agent to be used in the reduction include a metal reducing reagent such as sodium borohydride, lithium borohydride or lithium aluminum hydride, or diborane.

Examples of the solvent to be used in the reduction include water, methanol, ethanol, 1-propanol, 2-propanol, tert-butyl alcohol, tetrahydrofuran, dioxane, diethyl ether, ethylene glycol dimethyl ether or a mixture thereof.

The reaction temperature of the reduction is generally from -20 to 80° C. and a lower or higher temperature than the said temperature range may be selected on demand.

The reaction period of the reduction is generally from 30 minutes to 10 hours and a longer or shorter reaction period than the indicated period may be selected on demand.

After the reduction is carried out under the above-mentioned conditions or after removing the protecting group(s) on demand, the objective compound can be purified by a method known in the field of organic synthetic chemistry, such as solvent extraction, recrystallization, chromatography or a method using an ion exchange resin.

Examples of the reagent to be used in the deprotection include an acid such as hydrochloric acid, sulfuric acid, acetic acid or trifluoroacetic acid, a base such as sodium hydroxide, potassium hydroxide or lithium hydroxide.

Examples of the solvent to be used in the deprotection include water, methanol, ethanol, isopropyl alcohol, tert-butyl alcohol, acetone, tetrahydrofuran, ethylene glycol dimethyl ether, dimethylformamide or dimethyl sulfoxide.

The reaction temperature of the deprotection is generally from −20 to 100° C. and a lower or higher temperature than the said temperature range may be selected on demand.

The reaction period of the deprotection is generally from 30 minutes to 5 hours and a longer or shorter reaction period than the indicated period may be selected on demand.

After the deprotection is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method N

Compound (XXVI) can be also produced by reacting Compound (VIII) with formylating agent in the presence of magnesium, followed by hydrolysis.

Method O

Compound (I-a) of the present invention can be also produced by reacting and treating in the same manner as in Method E after condensing Compound (XXVIII) with Compound (XI), in the same manner as in Method F after condensing Compound (XXVIII) with Compound (XIII), in the same manner as in Method G after condensing Compound (XXVIII) with Compound (XV), in the same manner as in Method I after condensing Compound (XXVIII) with Compound (XIX), in the same manner as in Method J after condensing Compound (XXVIII) with Compound (XXII), respectively.

Compound (I) of the present invention is treated, in a suitable solvent such as water, methanol, ethanol, diethyl ether, tetrahydrofuran or dioxane if necessary, with an acid such as hydrochloric acid, hydrobromic acid, hydroiodic acid, sulfuric acid, nitric acid, phosphoric acid, acetic acid, maleic acid, fumalic acid, benzoic acid, citric acid, oxalic acid, succinic acid, tartaric acid, malic acid, mandelic acid, methanesulfonic acid, benzenesulfonic acid, p-toluenesulfonic acid or 10-camphorsulfonic acid to give an acid addition salt thereof. When the crystals of a compound of the present invention obtained are anhydrides, the crystals are treated with water, aqueous solvent or other solvent to give a hydrates such as monohydrate, ½ hydrate, ⅕ hydrate, dihydrate or 3/2 hydrate, or solvates.

Compound (I) of the present invention, a pharmaceutically acceptable acid addition salt thereof or a hydrate thereof can be used for the prevention and suppression of rejection caused by transplanting organ (liver, heart, kidney etc.) or bone marrow among the same kind or different kinds of mammals inclusive of human, dog, cat, cattle, horse, pig, monkey, rat etc., and for the prevention and treatment of various autoimmune diseases or various allergic diseases. Namely, the compounds of the present invention have pharmacological activities such as immunosuppressive activity or antimicrobial activity, and therefore are useful for the prevention or treatment of resistance to transplantation or transplantation rejection of organs or tissues (such as heart, kidney, liver, lung, bone marrow, cornea, pancreas, intestinum tenue, limb, muscle, nervus, fatty marrow, duodenum, skin or pancreatic islet cell etc., including xeno-transplantation), graft-versus-host diseases by bone marrow transplantation, autoimmune diseases such as rheumatoid arthritis, systemic lupus erythematosus, nephrotic syndrome lupus, Hashimoto's thyroiditis, multiple sclerosis, myasthenia gravis, type I diabetes mellitus, type II adult onset diabetes mellitus, uveitis, nephrotic syndrome, steroid-dependent and steroid-resistant nephrosis, palmoplantar pustulosis, allergic encephalomyelitis, glomerulonephritis, etc., and infectious diseases caused by pathogenic microorganisms.

The compounds of the present invention are useful for treating inflammatory, proliferative and hyperproliferative skin diseases and cutaneous manifestations of immunologically-mediated illnesses such as psoriasis, psoriatic arthritis, atopic eczema (atopic dermatitis), contact dermatitis and further eczematous dermatitises, seborrheic dermatitis, lichen planus, pemphigus, bullous pemphigoid, epidermolysis bullosa, urticaria, angioedema, vasculitis, erythema, cutaneous eosinophilia, acne, alopecia areata, eosinophilic fasciitis, and atherosclerosis.

More particularly, the compounds of the present invention are useful in hair revitalizing, such as in the treatment of female or male pattern alopecia, or senile alopecia, by providing epilation prevention, hair germination, and/or a promotion of hair generation and hair growth.

The compounds of the present invention are further useful in the treatment of respiratory diseases, for example, sarcoidosis, fibroid lung, idiopathic interstitial pneumonia, and reversible obstructive airways disease, including conditions such as asthma, including bronchial asthma, infantile asthma, allergic asthma, intrinsic asthma, extrinsic asthma and dust asthma, particularly chronic or inveterate asthma (for example late asthma and airway hyperresponsiveness), bronchitis and the like.

The compounds of the present invention may also be useful for treating hepatopathy associated with ischemia.

The compounds of the present invention are also indicated in certain eye diseases such as conjunctivitis, keratoconjunctivitis, keratitis, vernal conjunctivitis, uveitis associated with Behçet's disease, herpetic keratitis, conical cornea, dystorphia epithelialis corneae, keratoleukoma, ocular pemphigus, Mooren's ulcer, scleritis, Graves' ophthalmopathy, severe intraocular inflammation and the like.

The compounds of the present invention are also useful for preventing or treating inflammation of mucosa or blood vessels (such as leukotriene $B_4$-mediated diseases, gastric ulcers, vascular damage caused by ischemic diseases and thrombosis, ischemic bowel disease, inflammatory bowel disease (e.g. Crohn's disease and ulcerative colitis), necrotizing enterocolitis), or intestinal lesions associated with thermal burns.

Further, the compounds of the present invention are also useful for treating or preventing renal diseases including interstitial nephritis, Goodpasture's syndrome, hemolytic uremic syndrome and diabetic nephropathy; nervous diseases selected from multiple myositis, Guillain-Barré syndrome, Ménière's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, vitiligo vulgaris, ichthyosis vulgaris, photoallergic sensitivity and cutaneous T cell lymphoma; circulatory diseases including arteriosclerosis, aortitis, polyarteritis nodosa and myocardosis; collagen disease including scleroderma, Wegener's granuloma and Sjögren' syndrome; adiposis; eosinophilic fasciitis; periodontal disease; nephrotic syndrome; hemolytic uremic syndrome; and muscular dystrophy.

Further, the compounds of the present invention are indicated in the treatment of diseases including intestinal inflammations or allergies such as Coeliac disease, proctitis, eosinophilic gastroenteritis, mastocytosis, Crohn's disease or ulcerative colitis; and food related allergic diseases which have symptomatic manifestation remote from the gastrointestinal tract, for example migraine, rhinitis and eczema.

The compounds of the present invention also have liver regenerating activity and/or activity in promoting hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), viral hepatitis type B, non-A/non-B hepatitis and cirrhosis.

The compounds of the present invention are also indicated for use as antimicrobial agents, and thus may be used in the treatment of diseases caused by pathogenic microorganisms and the like.

Further, the compounds of the present invention can be used in the prevention or treatment of malignant rheumatoid arthritis, amyloidosis, fulminant hepatitis, Shy-Drager syndrome, pustular psoriasis, Behçet's disease, systemic lupus erythematosus, endocrine opthalmopathy, progressive systemic sclerosis, mixed connective tissue disease, aortitis syndrome, Wegener's gramulomatosis, active chronic hepatitis, Evans syndrome, pollinosis, idiopathic hypoparathyroidism, Addison disease (autoimmune adrenalitis), autoimmune orchitis, autoimmune oophoritis, cold hemagglutinin, paroxysmal cold hemoglobinuria, pernicious anemia, adult T cell leukemia, autoimmune atrophic gastritis, lupoid hepatitis, tubulointerstitial nephritis, membranous nephritis, amyotrophic lateral sclerosis, rheumatic fever, postmyocardial infarction syndrome and sympathetic ophthalmitis.

The compounds of the present invention have antifungal effect and are useful as an antifungal agent.

Moreover, the compounds of the present invention, pharmaceutically acceptable acid addition salts thereof or hydrates thereof can be used in combination with other immunosuppressant(s), steroid(s) (prednisolone, methylprednisolone, dexamethasone, hydrocortisone and the like) or nonsteroidal acid anti-inflammatory agent. As the other immunosuppressant, preferred is particularly selected from azathioprine, brequinar sodium, deoxyspergualin, mizoribine, 2-morpholinoethyl mycophenolate, cyclosporin, rapamycin, tacrolimus monohydrate, leflunomide and OKT-3.

When Compound (I) of the present invention thus obtained, a pharmaceutically acceptable acid addition salt thereof or a hydrate thereof is used as a medicament, Compound (I) is admixed with a pharmaceutically acceptable carrier (e.g., excipients, binders, disintegrators, correctives, corrigents, emulsifiers, diluents, solubilizers and the like) to give a pharmaceutical composition or a pharmaceutical agent (tablets, pills, capsules, granules, powders, syrups, emulsions, elixirs, suspensions, solutions, injections, transfusions or external preparations), which can be administered orally or parenterally. The pharmaceutical composition can be formulated into a pharmaceutical preparation by a conventional method. In the present specification, "parenterally" includes subcutaneous injection, intravenous injection, intramuscular injection, intraperitoneal injection, transfusion and topical administration (administration through the skin, eye, lung, bronchus, nose, rectum). The preparation for injection, such as a sterile aqueous or oily suspension for injection, can be prepared using a suitable dispersing agent or a wetting agent and a suspending agent, according to a method known in the pertinent field. The sterile preparation for injection may be a sterile injectable solution or suspension in a non-toxic diluent or solvent permitting parenteral administration, such as an aqueous solution. Examples of the vehicle and solvent which can be used include water, Ringer solution, isotonic saline and the like. In addition, sterile nonvolatile oil can be generally used as a solvent or a solvent for suspension. For this end, any nonvolatile oil or fatty acid can be used, inclusive of natural, synthetic or semi-synthetic fatty oil or fatty acid, and natural, synthetic or semi-synthetic mono, di or triglycerides. The solid dosage form for oral administration includes the above-mentioned ones such as powders, granules, tablets, pills, capsules and the like. In these dosage forms, the active ingredient is admixed with at least one additive such as sucrose, lactose, cellulose sugar, mannitol, maltitol, dextran, starches, agar, arginates, kichins, chitosans, pectins, tragacanth gums, gum arabic, gelatins, collagens, casein, albumin, synthetic or semi-synthetic polymers and glycerides. In these dosage forms, routine additives can be added, which may be inert diluents, lubricants such as magnesium stearate, preservatives such as parabens and sorbic acid, antioxidants such as ascorbic acid, $\alpha$-tocopherol and cysteine, disintegrators, binders, tackifiers, buffers, sweeteners, flavors, perfumes and the like. An enteric coating may be applied to tablets and pills. The liquid agents for oral administration may be pharmaceutically acceptable emulsions, syrups, elixirs, suspensions, solutions and the like, which may contain inert diluents (e.g., water), which are generally used in the pertinent field.

The external agent applicable to Compound (I) of the present invention, a pharmaceutically acceptable acid addition salt thereof or a hydrate thereof includes an ointment, a paste, a liniment, a lotion, a plaster, a cataplasm, an eye drop, an eye ointment, a suppository, a fomentation, an inhalant, a spray, an aerosol, a paint, a nasal drop, a cream, a tape, a patch and the like.

The external agent of the present invention contains the compound of the present invention in the form of a mixture with an organic or inorganic carrier or excipient, and, for example, can be used in the form of a solid, semi-solid or liquid pharmaceutical preparation.

The compound of the present invention can be mixed with, for example, a non-toxic and pharmaceutically acceptable carrier which is usually employed for obtaining an external preparation for topical administration. A carrier which can be used includes water, glucose, lactose, gum arabic, gelatin, mannitol, starch paste, magnesium trisilicate, talc, corn starch, keratin, colloid silica, potato starch, urea and other carriers which are suitable for preparing a solid, semi-solid or solution composition. Further, an adjuvant, a stabilizer, a thickener, a coloring matter or a flavoring agent can be added.

The compound of the present invention as an active ingredient of the pharmaceutical composition can be contained in an amount enough to exhibit the desired activity depending on the symptom or severity of the diseases. In the case of the treatment of the symptom and diseases induced by immune disorder, the compound of the present invention can be administered by way of a topical administration, an aerosol or a rectal administration in a form of a dosage unit composition which contains pharmaceutically acceptable and non-toxic carrier, adjuvant and excipient. In the treatment of reversible obstructive airways disease, the compound of the present invention is preferably administered to lung by an aerosol in a form of, particularly a powder or a solution.

The amount of the compound of the present invention which can be mixed with a carrier can vary depending on the host to be treated and a specified dosage form. The specified dose of the specified patient should be determined depending on the various factors such as age, body weight, the whole condition of health, sex, meal, time for administration, administration route, rate of excretion, combination of drug and the severity of the specified diseases under treatment.

When the compound of the present invention is used in the form of an ointment, it is contained in an amount of 0.01 to 10 w/w % in the ointment. The ointment base which can be used includes oleaginous base (a natural wax such as white beeswax or carnauba wax, a petroleum wax such as hard paraffin or microcrystalline wax, a hydrocarbon wax such as liquid paraffin, white petrolatum or yellow petrolatum, plastibase, zelen 50W, silicone, a vegetable oil, lard, beef tallow, a simple ointment or lead oleate plaster), an emulsion type ointment base (an oil in water type (O/W type) base such as a hydrophilic ointment or a vanishing cream or a water in oil type (W/O type) base such as a hydrophilic petrolatum, a purified lanolin, aquahole, eucelin, neoselin, an absorptive ointment, a hydrous lanolin, cold cream, a hydrophilic plastibase), a water-soluble base (a macrogol ointment or solbase) or a suspension type ointment base (a lyogel base, e.g., a hydrogel base such as a non-fat ointment, a gelbase or lotion; or a FAPG base (a suspension of a microparticle of an aliphatic alcohol such as stearyl alcohol or cetyl alcohol in propylene glycol), and these ointment bases can be used alone or in a combination of not less than two bases.

Further, when used as an ointment, the compound of the present invention is dissolved in a solubilizing and absorptive accelerating agent and added to the above-mentioned ointment base. The solubilizing and absorptive accelerating agent to be used means the agent in which the compound of the present invention is soluble at a concentration of at least not less than 0.01 w/w % and which can accelerate the absorption of the compound of the present invention from skin when formulated as an ointment, and includes a lower alkanediol (e.g., ethylene glycol, propylene glycol or butylene glycol), an alkylene carbonate (e.g., propylene carbonate or ethylene carbonate), an alkanedicarboxylic acid ester (e.g., dimethyl adipate, diethyl adipate, diisopropyl adipate, diethyl pimelate, diethyl sebacate or dipropyl sebacate), a higher alkanoic acid glycerin ester (e.g., monolaurate, dilaurate or trilaurate), a higher alkenoic acid glycerin ester (e.g., monooleate, dioleate or trioleate), a higher alkanoic acid alkyl ester (e.g., isopropyl myristate or ethyl myristate), a higher unsaturated alcohol (e.g., geraniol or oleyl alcohol) or an azacycloalkane (e.g., 1-dodecylazacycloheptan-2-one). These solubilizing and absorptive accelerating agents can be used alone or in a mixture of not less than two agents, and can be added at a sufficient amount to dissolve the compound of the present invention. The amount generally ranges from 2 parts by weight to 200 parts by weight per one part by weight of the compound of the present invention. The upper amount is limited not to deteriorate the physicochemical properties of the ointment.

The ointment which contains the compound of the present invention may contain, in addition to the above-mentioned ointment base, other additives such as an emulsifier (e.g., polyoxyethylene hydrogenated castor oil, glycerol monostearate, sorbitan sesquioleate or lauromacrogol); a suspending agent (e.g., polyethylene glycol, polyvinylpyrrolidone or sodium carboxymethylcellulose); an antioxidant (e.g., a phenol or a quinone); a preservative (e.g., paraoxybenzoic acid ester); a humectant (e.g., glycerin, D-sorbitol or propylene glycol); a favoring agent, a coloring matter; an antiseptic; a higher alkenoic acid (e.g., oleic acid), and moreover other drugs which are useful for the treatment of a skin diseases. When the compound of the present invention is used as ointment, the ointment can be prepared by mixing a solution containing the compound of the present invention with an ointment base in accordance with a conventional method. In the process of formulation, not less than one of the adjuvant or additive mentioned above can be simultaneously added to the ointment base. Furthermore, the ointment can be manufactured by dissolving the compound of the present invention in the solubilizing and absorptive accelerating agent, admixing the obtained solution with the ointment base, stirring the obtained mixture under heating, and then cooling the resultant mixture.

The ointment containing the compound of the present invention can be used by applying to the affected part of the skin once to several times (e.g., once to four times) a day.

The paste or liniment containing the compound of the present invention can be prepared by using the same base and according to the same method as those of the ointment as mentioned above.

The lotion containing the compound of the present invention means a preparation wherein the active ingredient compound is homogeneously dispersed or, in some cases, partially dissolved in a liquid medium, and an emulsifier can be added thereto as necessary. In a case where the compound of the present invention is used as a lotion, the content may be adjusted to 0.01 to 10 w/w % of the lotion.

The liquid medium to be used in the lotion containing the compound of the present invention includes water, a lower alcohol, a glycol, glycerin or a mixture thereof. Among them, all of the lower alcohols that do not decompose the active ingredient compound and are not irritant to skin can be used, and are inclusive methanol, ethanol, isopropyl alcohol, propanol or butanol. The glycol includes ethylene glycol, propylene glycol, butylene glycol or mono lower ethers thereof. Among these liquid media, water, the lower alcohol or a mixture thereof is most preferable because these media improve the absorption of the active ingredient compound to the skin. The amount of these liquid media preferably ranges from 5 parts by weight to 1000 parts by weight per one part by weight of the compound of the present invention.

To the lotion containing the compound of the present invention may be added a solubilizing and absorptive accelerating agent in which the active ingredient compound is soluble at a concentration of at least not less than 0.01 w/w % and which can accelerate the absorption of the active ingredient compound from the skin when formulated into a lotion, and includes an alkanedicarboxylic acid ester (e.g., dimethyl adipate, diethyl adipate, diisopropyl adipate, diethyl pimelate, diethyl sebacate or dipropyl sebacate) or a higher alkanoic acid alkyl ester (e.g., isopropyl myristate or ethyl myristate). These solubilizing and absorptive accelerating agents can be used alone or in a mixture of not less than two agents, and the amount generally ranges from 5 parts by weight to 5000 parts by weight per one part by weight of the compound of the present invention. The content of the solubilizing and absorptive accelerating agent desirably ranges from 1 to 30 w/w %.

The emulsifier for the lotion containing the compound of the present invention is employed for the purpose of dispersing an insoluble medicine minutely and homogeneously in an aqueous solution, and should be nontoxic to human beings, and includes pharmaceutically acceptable natural emulsifiers and synthetic emulsifiers. Various emulsifiers which are derived from animals and vegetables can be used as the natural emulsifier, and include egg yolk lecithin, soybean lecithin or a hydrogenated product thereof, phosphatidyl choline, sphingomyelin, gum arabic or gelatin. Cationic, anionic or non-ionic surfactants can be used as the synthetic emulsifier, and preferably include a castor oil surfactant, especially an HCO (polyoxyethylene hydrogenated castor oil) such as HCO-60, HCO-50, HCO-40. Further, a polyoxyethylenesorbitan aliphatic acid ester such as polysorbate 80, a glycerin aliphatic acid ester such as glycerin monocaprylate, a polyethylene aliphatic acid ester such as polyoxyethylene 40 monostearate, a middle chain aliphatic acid mono (or di)glyceride (e.g., C6–C12 aliphatic acid mono (or di)glycerides such as caprylic acid diglyceride, caprylic acid monoglyceride or caproic acid diglyceride) or a polyoxyethylated glyceride such as polyoxyethylated oleic acid glyceride.

The above-mentioned emulsifiers can be used as the primary emulsifier, and, if necessary, in combination with an auxiliary emulsifier. The auxiliary emulsifier is conventional and non-toxic to human beings, and includes cholesterol, agar, magnesium hydroxide, methylcellulose or pectin. These primary emulsifier and auxiliary emulsifier may be respectively used alone or in combination of two or more of them.

The emulsifier is contained in the lotion containing the compound of the present invention in an amount sufficient to emulsify the compound of the present invention and other additives to be contained, and preferably ranges from 0.1 part by weight to 10 parts by weight per one part by weight of the compound of the present invention.

In order to increase the viscosity, a viscosity-increasing agent may be added to the lotion which contains the compound of the present invention. The viscosity-increasing agent is any conventional agent which is usually added to give the viscosity to the liquid and is non-toxic to human beings, and includes carboxypolymethylene. The viscosity-increasing agent is used when the lotion with a high viscosity is desired. When the viscosity-increasing agent is used, the content of the viscosity-increasing agent may vary depending on the desired viscosity of the lotion to be used and preferably ranges from 0.01 to 5 w/w %.

The lotion which contains the compound of the present invention may further contain a solubilizer which is used for the stabilization of the active ingredient compound in an aqueous solution. If necessary, it may further contain other additives which are used for the lotion, such as a flavoring agent, a coloring matter, an antiseptic or a higher alkenoic acid such as oleic acid, or other drugs which are useful for the treatment of the skin diseases.

The lotion which contains the compound of the present invention may be prepared by a conventional method in this field. The lotion which contains the compound of the present invention can be used by applying to the affected part of the skin once to several times (e.g., once to four times) a day. When the lotion has a low viscosity, it can be applied by filling a spray vessel with the composition of the lotion and spraying the lotion directly to the skin.

In case where the compound of the present invention is used in the form of an eye drop or a nasal drop, the solvent to be employed includes a sterile distilled water or, in particular a distilled water for injection. The concentration of the active compound usually ranges from 0.01 to 2.0 w/v %, and may be increased or decreased depending on the aim of use.

The eye drop or nasal drop which contains the compound of the present invention may further contain various additives such as a buffer, an isotonic agent, a solubilizing agent, a preservative, a viscosity-increasing agent, a chelating agent, a pH adjustor or an aromatic.

The buffer includes, for example, a phosphate buffer (e.g., sodium dihydrogen phosphate-disodium hydrogen phosphate or potassium dihydrogen phosphate-potassium hydroxide), a borate buffer (e.g., boric acid-borax), a citrate buffer (e.g., sodium citrate-sodium hydroxide), a tartrate buffer (e.g., tartaric acid-sodium tartrate), an acetate buffer (e.g., acetic acid-sodium acetate), a carbonate buffer (e.g., sodium carbonate-citrate or sodium carbonate-boric acid) or an amino acid (e.g., sodium glutamate or ε-aminocaproic acid).

The isotonic agent includes a saccharide such as sorbitol, glucose or mannitol, a polyhydric alcohol such as glycerin or propylene glycol, a salt such as sodium chloride or borax, or boric acid and the like.

The solubilizing agent includes a non-ionic surfactant such as polyoxyethylene sorbitan monooleate (polysorbate 80), polyoxyethylene monostearate, polyethylene glycol or polyoxyethylene hydrogenated castor oil and the like. The preservative includes, for example, a quaternary ammonium salt such as benzalkonium chloride, benzethonium chloride or cetylpyridinium chloride, a parahydroxybenzoic acid ester such as methyl parahydroxybenzoate, ethyl parahydroxybenzoate, propyl parahydroxybenzoate or butyl parahydroxybenzoate, benzyl alcohol, phenethyl alcohol, sorbic acid or a salt thereof, thimerosal, chlorobutanol or sodium dehydroacetate.

The viscosity-increasing agent includes, for example, polyvinylpyrrolidone, hydroxyethylcellulose, hydroxypropylcellulose, methylcellulose, hydroxypropylmethylcellulose, or carboxymethylcellulose or a salt thereof. The chelating agent includes sodium edetate or citric acid and the like. The pH adjustor includes hydrochloric acid, citric acid, phosphoric acid, acetic acid, tartaric acid, sodium hydroxide, potassium hydroxide, sodium carbonate or sodium bicarbonate and the like. The aromatic includes l-menthol, borneol, a camphor (e.g., dl-camphor) or eucalyptus oil and the like.

When the compound of the present invention is used as an eye drop, it may be usually adjusted to from about 4.0 to about 8.5 of pH, and when using as a nasal drop, it may be usually adjusted to from about 4.0 to about 8.5 of pH.

The manufacture of the eye drop and the nasal drop which contain the compound of the present invention can apply a method known in each preparation itself, while depending on the kind of each preparation.

When the compound of the present invention is used as an eye drop, it may contain an active ingredient in a sufficient amount to be able to effectively prevent the eye inflammation, which may vary depending on the symptom or the sort of inflammation, and usually ranges from about 5.0 to about 1000 μg for one administration. It may be administered once to several times (e.g., once to four times) a day.

The aerosol containing the compound of the present invention means a pharmaceutical preparation which can be applied at the time of treatment by spraying a solution or a suspension of the active ingredient compound using a pressure of a liquefied gas or compressed gas filled in the same vessel or another vessel. The aerosol can be prepared by dissolving the compound of the present invention in a purified water, and, if necessary, dissolving or suspending the same solubilizing and absorptive accelerating agent as mentioned above in the solution, and, if necessary, adding an additive such as pH adjustor or antiseptic as mentioned above, and then sealing closely with a valve and compressing the propellant.

The propellant to be used includes dimethyl ether, liquefied natural gas, carbon dioxide, nitrogen gas, a substituted from gas and other conventional propellants.

The aerosol which contains the compound of the present invention may further contain a refrigerant such as 1-menthol, a camphor, methyl salicylate and the like.

The inhalant or spray which contains the compound of the present invention can be prepared according to the same methods as those mentioned in aerosol, a nebulizer or an inhaler can be used for inhalant and a spraying vessel can be used for spray.

When the compound of the present invention is used as a suppository, the suppository can be prepared in a conventional manner using a conventional base for suppository, and the active ingredient compound is contained in the suppository in an amount sufficient to exhibit the pharmaceutical effect, which can vary depending on the age or symptom of the patient, and preferably ranges from 0.1 to 60 mg.

The base for suppository of the present invention is the conventional base, and includes an oil and fat from animal and vegetable such as olive oil, corn oil, castor oil, cotton seed oil, wheat germ oil, cacao oil, beef tallow, lard, wool fat, turtle tallow, squalane or a hydrogenated oil, an oil and fat from mineral such as petrolatum, white petrolatum, hard paraffin, liquid paraffin, anhydrous lanolin or silicone oil, a wax such as jojoba oil, carnauba wax, yellow beeswax or lanolin, a partially synthetic or totally synthetic glycerin aliphatic acid ester such as mono, di and triglycerides of a middle or higher aliphatic acid such as a straight-chain saturated aliphatic acid (e.g., lauric acid, myristic acid, palmitic acid or stearic acid), or a straight-chain unsaturated aliphatic acid (e.g., oleic acid, linoleic acid or linolenic acid). The commercially available products are exemplified by Witepsol [manufactured by Dynamitnobel Co.; a mixture of mono-, di- and triglycerides of C12–C18 saturated aliphatic acid, in more detail, Witepsol H series (e.g., Witepsol H5, H12, H19, H32, H35, H37, H39, H42, H175 or H185), Witepsol W series (e.g., Witepsol W25, W31, W35 or W45), Witepsol E series (e.g., Witepsol E75, E76, E79 or E85) or Witepsol S series (e.g., Witepsol S52, S55 or S58) are included]; Pharmasol (manufactured by Nippon Oils and Fats Co.); Isocacao (manufactured by Kao Co.); SB (manufactured by Kanegafuchi Chemical Co. and Taiyo Yusi Co.; a mixture of mono-, di- and tri-glycerides of C12–C18 saturated aliphatic acid, in more detail, SB-H, SB-E or SB-AM are included); Nopata (manufactured by Henkel AG.); Sapoyer (manufactured by Gattfords Co.; a mixture of mono-, di- and tri-glycerides of C10–C18 saturated aliphatic acid, in more detail, Sapoyer NA, Sapoyer OS, Sapoyer AS, Sapoyer BS, Sapoyer BM or Sapoyer DM are included); Masaesthalinum (manufactured by Dynamitnobel Co.; a mixture of mono-, di- and tri-glycerides of C10–C18 saturated aliphatic acid, in more detail, Masaesthalinum A, AB, B, BB, BC, BCF, C, D, E or BD and Masaesthalinum 299 are included); or Migriol 810 or Migriol 812 (manufactured by Dynamitnobel Co.; a mixture of triglycerides of C8–C12 saturated aliphatic acid, in more detail, one or more of them may optionally be incorporated when the partially synthetic or totally synthetic glycerin aliphatic acid ester as mentioned above are incorporated). Further, other synthetic products such s polyethylene glycol or polyoxyethylene alcohol can be exemplified. The bases are used in an amount of 25 to 99.9% by weight based on the total weight of the suppository.

To the suppository containing the compound of the present invention may be added, if necessary, a preservative, a stabilizer, a surfactant, an aromatic, a pH adjustor or a purified water.

The suppository containing the compound of the present invention may be in various forms such as a rectal suppository which is solid at the normal temperature and melts at a body temperature; an ointment or liquid enema which can be prepared by dissolving or dispersing the compound of the present invention in a liquid base; a soft capsule for the rectal administration; or an injection for the rectal administration.

The manufacture of the suppository which contains the compound of the present invention is carried out using a method known in this field.

While the dose for a certain patient is determined according to age, body weight, general health conditions, sex, diet, administration time, administration route, clearance rate, combination of drugs, degree of the state of the disease for which the patient is then undergoing treatments, and other factors. The compound of the present invention, a pharmaceutically acceptable acid addition salt thereof and a salt thereof show low toxicity and can be used safely. While the daily dose varies depending on the condition and body weight of the patient, the kind of compound and administration route and the like, it is, for example, about 0.01–50 mg/person/day, preferably 0.01–20 mg/person/day, for parenteral administration by a subcutaneous, intravenous or intramuscular route, or through the skin, eye, lung, bronchus, nose or rectum, and about 0.01–150 mg/person/day, preferably 0.1–100 mg/person/day, for oral administration.

Compound A useful as a synthetic intermediate for Compound (I) of the present invention is also useful as a synthetic intermediate for a compound of the general formula (II-a) [hereinafter referred to as Compound (II-a)], in which Compound (I) of the present invention is encompassed,

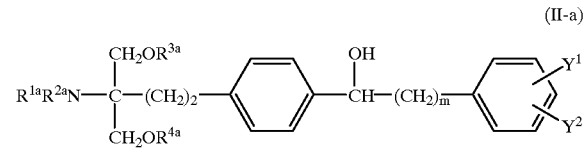

(II-a)

wherein m is 0 to 9, preferably 4, and $R^{1a}$, $R^{2a}$, $R^{3a}$ and $R^{4a}$ are the same or different and each is a hydrogen, an acyl (a straight- or branched chain alkanoyl having 1 to 20 carbon atoms such as formyl, acetyl, propionyl, butyryl, isobutyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl and the like; a straight- or branched chain alkanoyl having 2 to 20 carbon atoms which may be substituted by phenyl, such as phenylacetyl, phenylpropionyl and the like; an aroyl such as benzoyl and the like; a straight- or branched chain alkoxycarbonyl wherein the alkoxy moiety has 1 to 20 carbon atoms, such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, tert-pentyloxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl, tridecyloxycarbonyl, tetradecyloxycarbonyl, pentadecyloxycarbonyl, hexadecyloxycarbonyl, heptadecyloxycarbonyl, octadecyloxycarbonyl, nonadecyloxycarbonyl, icosyloxycarbonyl and the like; aralkyloxycarbonyl such as benzyloxycarbonyl and the like), or an alkyl (a straight- or branched chain alkyl having 1 to 20 carbon atoms, such as methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl and the like) or $R^{3a}$ and $R^{4a}$ may be combined by an alkylene chain which may be substituted by an alkyl having 1 to 4 carbon atoms as the above-mentioned, an aryl such as phenyl and the like or an aralkyl such as benzyl and the like, and $Y^1$ and $Y^2$ are the same or different and each is a hydrogen, an alkyl having 1 to 4 carbon atoms as above-mentioned, an alkoxy having 1 to 4 carbon atoms (methoxy, ethoxy, propoxy, isopropoxy, butoxy, isobutoxy, tert-butoxy and the like), halogen (fluorine, chlorine, bromine, iodine) or hydroxyl group, and as a synthetic intermediate of a compound of the general formula (I-c) [hereinafter referred to as Compound (I-c)]

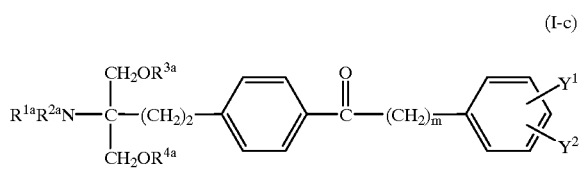
(I-c)

wherein m, $R^{1a}$, $R^{2a}$, $R^{3a}$, $R^{4a}$, $Y^1$ and $Y^2$ are as defined above, which is produced by oxidizing Compound (II-a) with a suitable oxidizing agent. The compound wherein, in the carbon chain at the 2-position of 2-amino-1,3-propanediol skeleton, the p-phenylene group in the carbon chain and the phenyl group at the end of the carbon chain are substituted and, in the carbon chain between the said p-phenylene group and the said phenyl group, the carbon atom at the a-position of the p-phenylene group is substituted by a carbonyl group, which is represented by Compound (I-c), shows less toxicity and high safety, and is useful as a superior immunosuppressant, like the compound of the present invention. Compound (II-a) is useful as a synthetic intermediate of Compound (I-c), also shows less toxicity and higher safety, and is useful as a superior immunosuppressant, like Compound (I-c).

Compound (II-a) and Compound (I-c) can be produced by reacting and treating a compound of the general formula (XXX) [hereinafter referred to as Compound (XXX)]

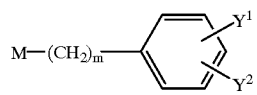
(XXX)

wherein M, m, $Y^1$ and $Y^2$ are as defined above, instead of Compound (III) in Method A, with the amino- and/or hydroxy-protected Compound A according to Method A and Method B. Further, by reacting and treating in the same manner using an alkyl halide instead of an acyl halide in Method B, the corresponding amino- and/or hydroxy-alkylated compound can be produced. Moreover, by reacting and treating in the same manner using Compound (XXX) instead of Compound (III) in Method M, Compound (I-c) can be also produced.

Compound (II-a) and Compound (I-c) obtained can be converted into an acid addition salt thereof, a hydrate thereof and the like in the same manner mentioned above.

In Compound (II-a), a compound of the general formula (II-b) [hereinafter referred to as Compound (II-b)]

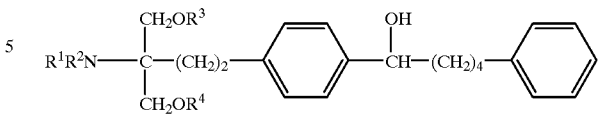
(II-b)

wherein $R^1$, $R^2$, $R^3$ and $R^4$ are as defined above, is preferable and 2-amino-2-(2-(4-(1-hydroxy-5-phenylpentyl)phenyl)ethyl)propane-1,3-diol is particularly preferable. In Compound (I-c), Compound (I)

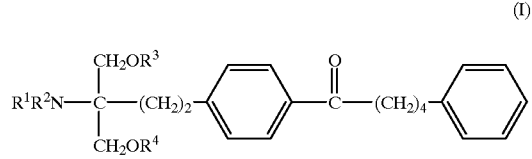
(I)

wherein $R^1$, $R^2$, $R^3$ and $R^4$ are as defined above, is preferable and 2-amino-2(2-(4-(1-oxo-5-phenylpentyl)phenyl)ethyl)propane-1,3-diol is particularly preferable.

Moreover, instead of Compound (XXX), a compound of the general formula (XXI) [hereinafter referred to as Compound (XXXI)]

M—(CH$_2$)$_n$CH$_3$ (XXXI)

wherein n is a integer of 0 to 12, preferably 6, and M is as defined above, is reacted and treated with amino- and/or hydroxy-protected Compound A according to Method A and Method B [containing the method reacting and treating in the same manner using an alkyl halide instead of an acyl halide in Method B], or reacted and treated using Compound (XXXI) instead of Compound (III) in Method M to produce a compound of the general formula (XXII) or (XXXIII) [hereinafter referred to as Compound (XXXII) and Compound (XXXIII)]

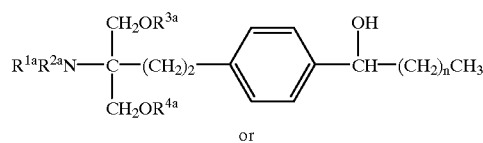
(XXXII)

or

(XXXIII)

wherein $R^{1a}$, $R^{2a}$, $R^{3a}$, $R^{4a}$ and n are as defined above. Compound (XXXII) and Compound (XXXIII) obtained are respectively show less toxicity and higher safety, and is useful as a superior immunosuppressant, like Compound (I) of the present invention.

DESCRIPTION OF THE PREFERRED EMBODIMENTS

Figure 1:
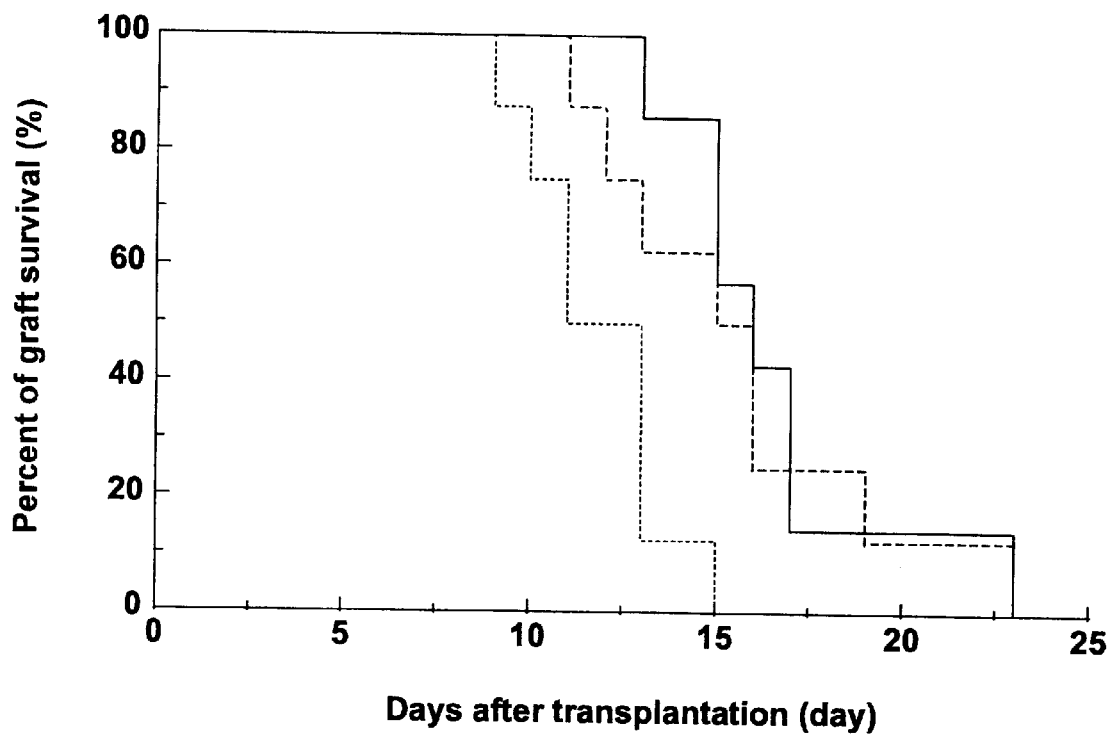
FIG. 1 is a graph which shows the results of Experimental Example 12, wherein . . . shows the result of comparative compound 1, - - - shows the result of comparative compound 2 and — shows the result of Compound (I-a) of the present invention.

The present invention is hereinafter explained in detail by illustrating examples, to which the present invention is construed not to be limited. Of the symbols used in the formula, Ac is acetyl, Et is ethyl, TBDMS is tert-butyldimethylsilyl.

WORKING EXAMPLE 1
Synthesis of 2-amino-2-(2-(4-(1-oxo-5phenylpentyl)phenyl)ethyl)propane-1,3-diol
(1) Synthesis of diethyl 2-acetamido-2-(2-phenylethyl)malonate

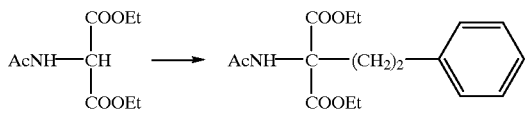

To a suspension of sodium hydride (50.6 g) in dimethylformamide (1500 ml) was dropwise added a solution of diethyl acetamidomalonate (250 g) in dimethylforamide (200 ml) under ice-cooling, and the mixture was stirred at room temperature for 30 minutes. 2-Phenylethyl bromide (156 ml) was dropwise added thereto and the resultant mixture was stirred for 7 hours at room temperature. The reaction mixture was poured into ice water (1500 ml) and extracted with ethyl acetate. The ethyl acetate layer was washed with water, dried over anhydrous magnesium sulfate and the solvent was distilled away. The obtained residue was crystallized from toluene to give the title compound (102 g) as white crystals, melting point 115–117° C.

$^1$H-NMR (CDCl$_3$) δ: 1.25 (6H, t, J=7.3 Hz), 1.97 (3H, s), 2.48 (1H, d, J=11.2 Hz), 2.50 (1H, d, J=9.2 Hz), 2.69 (1H, d, J=9.2 Hz), 2.71 (1H, d, J=11.2 Hz), 4.19 (4H, q, J=7.3 Hz), 6.77 (1H, s), 7.13–7.20 (3H, m), 7.20–7.30 (2H, m)

IR(KBr): 3236, 1745, 1635 cm$^{-1}$
MS(EI): 321 (M$^+$)
elemental analysis: C$_{17}$H$_{23}$NO$_5$ calculated C; 63.54, H; 7.21, N; 4.36 found C; 63.44, H; 7.29, N; 4.44

(2) Synthesis of 2-acetamido-1,3-diacetoxy-2-(2-phenylethyl)propane

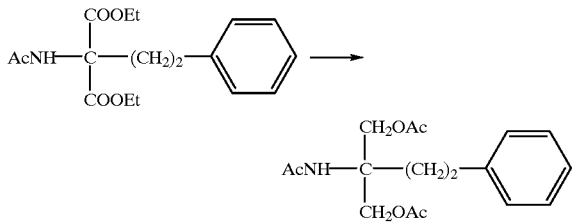

To a solution of lithium aluminum hydride (11.8 g) in anhydrous tetrahydrofuran (1500 ml) was dropwise added a solution of diethyl 2acetamido-2-(2-phenylethyl)malonate (50 g) in anhydrous tetrahydrofuran (300 ml) under ice-cooling, and the mixture was stirred at room temperature for 2 hours. A saturated aqueous sodium sulfate solution (150 ml) was dropwise added thereto to decompose lithium aluminum hydride. The precipitate was filtered off with celite and the solvent was distilled away under reduced pressure to give a pale brown oily substance. This was dissolved in pyridine (90 ml), acetic anhydride (70 ml) was added thereto and the mixture was allowed to stand overnight at room temperature. The reaction mixture was poured into water and extracted with ethyl acetate. The ethyl acetate layer was washed with a saturated aqueous ammonium chloride solution, dried over anhydrous magnesium sulfate and the solvent was distilled away under reduced pressure. The obtained residue was crystallized from toluene to give the title compound (29.3 g) as white crystals, melting point 116–117° C.

$^1$H-NMR (CDCl$_3$) δ: 1.96 (3H, s), 2.09 (6H, s), 2.20 (2H, m), 2.64 (2H, m), 4.35 (4H, s), 5.69 (1H, s), 7.10–7.20 (3H, m), 7.20–7.30 (2H, m)

IR(KBr): 3315, 1732, 1652 cm$^{-1}$
MS(EI): 321 (M$^+$)
elemental analysis : C$_{17}$H$_{23}$NO$_5$ calculated C; 63.54, H; 7.21, N; 4.36 found C; 63.37, H; 7.30, N; 4.35

(3) Synthesis of 2-acetamido-1,3-diacetoxy-2-(2-(4-formylphenyl)ethyl)propane

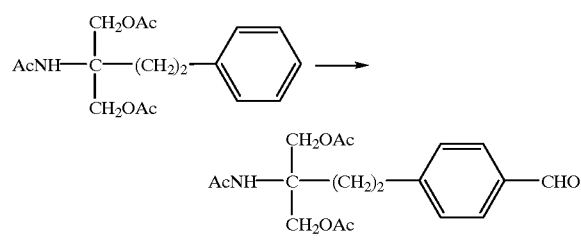

To a solution of 2-acetamido-1, 3-diacetoxy-2-(2-phenylethyl)propane (10 g) in anhydrous dichloromethane (150 ml) were added titanium tetrachloride (15.4 ml) and dichloromethyl methyl ether (5.63 ml) under a nitrogen atmosphere at −15° C. The mixture was stirred at room temperature for 2 hours, poured into ice water and extracted with chloroform. The chloroform layer was washed with water, a saturated aqueous sodium hydrogencarbonate solution and saturated brine, dried over anhydrous magnesium sulfate and the solvent was distilled away under reduced pressure. The obtained residue was purified by silica gel column chromatography (eluent; diisopropyl ether: ethyl acetate =1:1) to give the title compound (5.1 g) as a white solid, melting point 98–100° C.

$^1$H-NMR (CDCl$_3$) δ: 1.99 (3H, s), 2.10 (6H, s), 2.25 (2H, m), 2.70 (2H, m), 4.34 (4H, s), 5.82 (1H, s), 7.35 (2H, d, J=7.9 Hz), 7.80 (2H, d, J=7.9 Hz), 9.97 (1H, S) IR(KBr): 3313, 3205, 3082, 1735, 1706, 1652 cm$^{-1}$

MS(EI): 349 (M$^+$)
elemental analysis: C$_{18}$H$_{23}$NO$_6$.⅓H$_2$O
calculated C; 61.25, H; 6.68, N; 3.97 found C; 61.40, H; 6.70, N; 3.96

(4) Synthesis of 2-acetamido-2-(2-(4-formylphenyl)ethyl)propane-1,3-diol

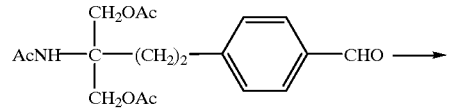

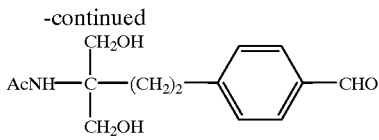

To a solution of 2-acetamido-1,3-diacetoxy-2-(2-(4-formylphenylethyl)propane (3.4 g) in ethanol (100 ml) was added sodium ethoxide (1.46 g) and the mixture was stirred at room temperature for 1.5 hours. The reaction mixture was concentrated, poured into ice water and extracted with ethyl acetate. The ethyl acetate layer was washed with saturated brine, dried over anhydrous magnesium sulfate and the solvent was distilled away under reduced pressure. The obtained residue was purified by silica gel column chromatography (eluent; chloroform: methanol=9:1) to give the title compound (1.7 g) as a pale yellow oily substance.

$^1$H-NMR (CDCl$_3$) δ: 2.00 (2H, m), 2.01 (3H, s), 2.70 (2H, m), 3.70–3.90 (4H, m), 4.45 (2H, brs), 6.36 (1H, s), 7.35 (2H, d, J=7.9 Hz), 7.77 (2H, d, J=7.9 Hz), 9.94 (1H, s)

MS(EI): 265 (M$^+$)

(5) Synthesis of 2-acetamido-1,3-bis(tert-butyldimethylsilyloxy)-2-(2-(4formylphenyl)ethyl)propane

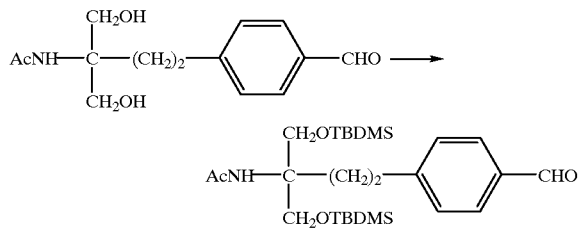

To a solution of 2-acetamido-2-(2-(4-formylphenyl)ethyl) propane-1,3-diol (9.7 g) in dimethylformamide (150 ml) were added imidazole (5.36 g) and tert-butyldimethylchlorosilane (11.9 g) and the mixture was stirred at room temperature for 2 hours. The reaction mixture was poured into water (200 ml) and extracted with ethyl acetate. The ethyl acetate layer was washed with saturated brine, dried over anhydrous magnesium sulfate and the solvent was distilled away under reduced pressure. The obtained residue was purified by silica gel column chromatography (eluent; hexane: ethyl acetate =4:1) to give the title compound (13.5 g) as a pale yellow oily substance.

$^1$H-NMR (CDCl$_3$) δ: 0.07 (12H, s), 0.90 (18H, s), 1.95 (3H, s), 2.14 (2H, m), 2.68 (2H, m), 3.66 (2H, d, J=9.9 Hz), 3.78 (2H, d, J=9.9 Hz), 5.60 (1H, s), 7.36 (2H, d, J=7.9 Hz), 7.78 (2H, d, J=7.9 Hz), 9.96 (1H, s)

IR(neat): 3365, 3087, 2954, 1702 cm$^-$

MS(EI): 493 (M$^+$)

elemental analysis: C$_{26}$H$_{47}$NO$_4$ Si$_2$·⅓H$_2$O calculated C; 62.78, H; 9.60, N; 2.82 found C; 62.59, H; 9.64, N; 2.66

(6) Synthesis of 2-acetamido-1,3-bis(tert-butyldimethylsilyloxy)-2-(2-(4-(1hydroxy-5-phenylpentyl) phenyl)ethyl)propane

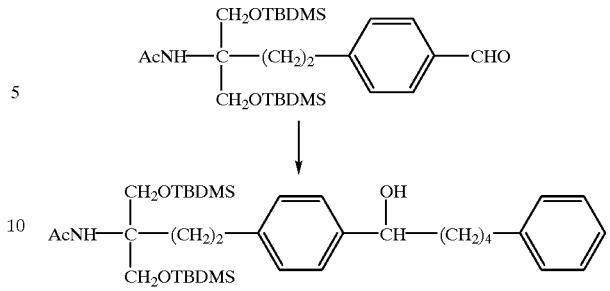

To a solution of magnesium (0.27 g) in anhydrous tetrahydrofuran (5 ml) was dropwise added a solution of 1-bromo-4-phenylbutane (2.35 g) in anhydrous tetrahydrofuran (5 ml) under a nitrogen atmosphere, and the mixture was stirred for 1.5 hours. To this solution was dropwise added a solution of 2-acetamido-1,3-bis(tert-butyldimethylsilyloxy)-2-(2-(4-formylphenyl)ethyl)propane (1.2 g) in anhydrous tetrahydrofuran (15 ml) and the mixture was stirred for 1 hour. 3% Hydrochloric acid was poured into the reaction mixture and the mixture was extracted with ethyl acetate. The ethyl acetate layer was washed with saturated brine, dried over anhydrous magnesium sulfate and the solvent was distilled away under reduced pressure. The obtained residue was purified by silica gel column chromatography (eluent; hexane: ethyl acetate=2:1) to give the title compound (1.27 g) as a colorless transparent oily substance.

$^1$H-NMR (CDCl$_3$) δ: 0.06 (12H, s), 0.90 (18H, s), 1.20–1.80 (7H, m), 1.87 (3H, s), 2.05 (2H, m), 2.50–2.60 (4H, m), 3.61 (2H, d, J=9.9 Hz), 3.72 (2H, d, J=9.9 Hz), 4.55 (1H, t, J=5.9 Hz), 5.50 (1H, s), 7.00–7.20 (9H, m)

IR(neat): 3296, 3086, 3062, 1657 cm$^{-1}$

MS(EI): 570 ((M-AcNH)$^+$)

(7) Synthesis of 2-acetamido-1,3-bis(tert-butyldimethylsilyloxy)-2-(2-(4-(1-oxo-5-phenylpentyl) phenyl)ethyl)propane

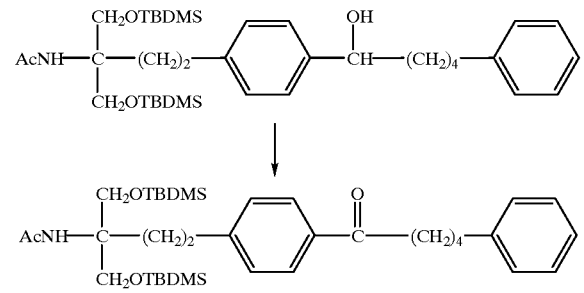

To a solution of dimethyl sulfoxide (0.73 ml) in dichloromethane (8 ml) was added oxalyl chloride (0.23 ml) under a nitrogen atmosphere at −78° C., and then 2-acetamido-1,3-bis(tert-butyldimethylsilyloxy)-2-(2-(4-(1-hydroxy-5-phenylpentyl)phenyl)ethyl)propane (1.1 g) in dichloromethane (7 ml), and the mixture was stirred at said temperature for 1 hour. Then, triethylamine (1.2 ml) was added thereto and the temperature of the mixture was raised to room temperature. The reaction mixture was poured into water and the mixture was extracted with chloroform. The chloroform layer was washed with saturated brine, dried over anhydrous magnesium sulfate and the solvent was distilled away under reduced pressure. The obtained residue was purified by silica gel column chromatography (eluent;

hexane: ethyl acetate=4:1) to give the title compound (0.91 g) as a colorless transparent oily substance.

$^1$H-NMR (CDCl$_3$) δ: 0.06 (12H, s), 0.90 (18H, s), 1.65–1.85 (4H, m), 1.95 (3H, 8), 2.14 (2H, m), 2.60–2.70 (4H, m), 2.95 (2H, t, J=7.3 Hz), 3.66 (2H, d, J=9.3 Hz), 3.78 (2H, d, J=9.3 Hz), 5.58 (1H, s), 7.10–7.20 (3H, m), 7.20–7.30 (4H, m), 7.84 (2H, d, J=8.6 Hz)

IR(neat): 3313, 1741, 1684 cm$^{-1}$

MS(EI): 568 ((M—AcNH)$^+$)

elemental analysis : C$_{36}$H$_{59}$NO$_4$Si$_2$·½H$_2$O calculated C; 68.09, H; 9.52, N; 2.21 found C; 68.05, H; 9.54, N; 2.19

(8) Synthesis of 2-amino-2-(2-(4-(1-oxo-5-phenylpentyl)phenyl)ethyl)propane- 1,3-diol

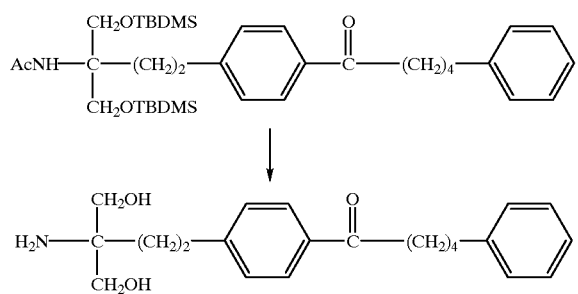

To a solution of 2-acetamido-1,3-bis(tert-butyldimethylsilyloxy)-2-(2-(4-(1-oxo-5-phenylpentyl)phenyl)ethyl)propane (0.9 g) in tetrahydrofuran (10 ml) was added a solution of tetra-n-butylammonium fluoride (1.2 g) in tetrahydrofuran (5 ml) under ice-cooling, and the mixture was stirred at room temperature for 1 hour. The reaction mixture was poured into water and extracted with ethyl acetate. The ethyl acetate layer was washed with saturated brine, dried over anhydrous magnesium sulfate and the solvent was distilled away under reduced pressure to give 2-acetamido-2-(2-(4-(1-oxo-5-phenylpentyl)phenyl)ethyl)propane-1,3-diol as a residue. The obtained residue was dissolved in water (5 ml)—methanol (5 ml)—tetrahydrofuran (3 ml), and lithium hydroxide monohydrate (0.3 g) was added thereto. The mixture was refluxed under heating for 1.5 hours. The reaction mixture was poured into water and extracted with ethyl acetate. The ethyl acetate layer was washed with saturated brine, dried over anhydrous magnesium sulfate and the solvent was distilled away under reduced pressure to give a white solid. The obtained white solid was recrystallized from ethanol-ethyl acetate-hexane to give the title compound (220 mg) as white crystals, melting point 126–127° C.

$^1$H-NMR (CDCl$_3$) δ: 1.60–1.80 (6H, m), 2.00 (4H, brs), 2.60–2.75 (4H, m), 2.95 (2H, t, J=7.2 Hz), 3.50–3.65 (4H, m), 7.10–7.15 (3H, m), 7.20–7.25 (4H, m), 7.86 (2H, d, J=7.9 Hz)

IR(KBr): 3349, 3290, 3025, 1678 cm$^{-1}$

MS(EI): 355 (M$^+$)

elemental analysis : C$_{22}$H$_{29}$NO$_3$ calculated C; 74.33, H; 8.22, N; 3.94 found C; 74.17, H; 8.29, N; 3.87

WORKING EXAMPLE 2

Synthesis of 2-amino-2-(2-(4-(1-oxo-5-phenylpentyl)phenyl)ethyl)propane-1,3-diol (other method)

(1) Synthesis of 4-(2-bromoethyl)benzaldehyde

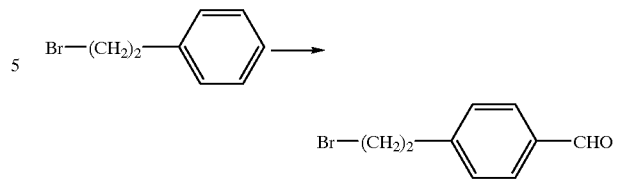

To a solution of dichloromethyl methyl ether (62 ml) in methylene chloride (40 ml) was added titanium tetrachloride (75 ml) over 10 minutes under a nitrogen atmosphere at 4–5° C. Then, a solution of phenethyl bromide (85 ml) in methylene chloride (50 ml) was added thereto over 50 minutes at 5–7° C. and the mixture was stirred for 5 hours while gradually raising the temperature of the mixture to room temperature. Water (200 ml) was added to the reaction mixture over 1 hour and the mixture was extracted with chloroform (200 ml). The chloroform layer was washed with water, a saturated aqueous sodium bicarbonate solution and saturated brine, dried over anhydrous sodium sulfate and the solvent was distilled away under reduced pressure to give a brown oily substance (167 g). The obtained brown oily substance was purified by silica gel column chromatography (eluent; hexane: ethyl acetate=20:1) to give 4-(2-bromoethyl)benzaldehyde (32.3 g) as a yellow solid, melting point 50–52° C.

$^1$H-NMR (270 MHz/CDCl$_3$) δ: 3.25 (2H, t, J=7.3 Hz), 3.61 (2H, t, J=7.3 Hz), 7.39 (2H, d, J=7.9 Hz), 7.84 (2H, d, J=7.9 Hz), 9.99 (1H, 9)

MS (EI) m/z 213 (M$^+$)

(2) Synthesis of 1-[4-(2-bromoethyl)phenyl]-5-phenylpentan-1-ol

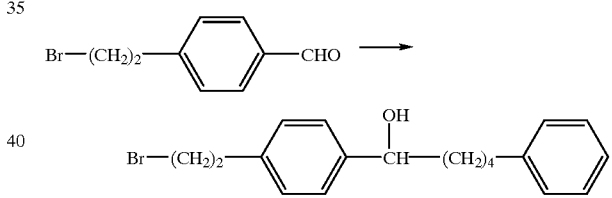

To a solution of magnesium (4.4 g) in tetrahydrofuran (20 ml) was added dibromoethane (1.6 ml) under a nitrogen atmosphere, and the mixture was stirred for 10 minutes. To the reaction mixture was added a solution of 1-bromo-4-phenylbutane (38.8 g) in tetrahydrofuran (30 ml) over 30 minutes, and the mixture was stirred for 40 minutes. The obtained Grignard reagent was dropwise added to a solution of 4-(2-bromoethyl)benzaldehyde (32.3 g) in tetrahydrofuran (250 ml) under ice-cooling over 30 minutes and the mixture was stirred at room temperature for 2 hours. To the reaction mixture was added a saturated aqueous ammonium chloride solution (200 ml) under ice-cooling, and the mixture was extracted with ethyl acetate (200 ml). The ethyl acetate layer was washed with saturated brine, dried over anhydrous magnesium sulfate and the solvent was distilled away under reduced pressure to give a brown oily substance (70.5 g). The obtained brown oily substance was purified by silica gel column chromatography (eluent; hexane: ethyl acetate=10:1) to give 1-[4-(2-bromoethyl)phenyl]-5-phenylpentan-1-ol (32 g) as a yellow oily substance.

$^1$H-NMR (270 MHz/CDCl$_3$) δ: 1.30–1.90 (7H, m), 2.59 (2H, t, J=7.3 Hz), 3.15 (2H, t, J=7.3 Hz), 3.55 (2H, t, J=7.3 Hz), 4.65 (1H, dt, J=2.0, 5.3 Hz), 7.10–7.20 (5H, m), 7.20–7.35 (4H, m)

MS (EI) m/z 330((M-17)$^+$)

(3) Synthesis of 1-[4-(2-bromoethyl)phenyl]-5-phenylpentan-1-one

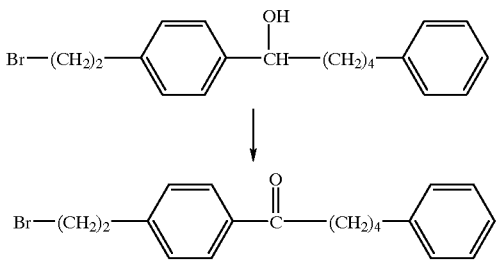

To a solution of dimethy sulfoxide (12.7 ml) in methylene chloride (320 ml) was added a solution of oxalyl chloride (7.7 ml) in methylene chloride (320 ml) over 10 minutes under a nitrogen atmosphere at −68 to −65° C., and the mixture was stirred at the said temperature for 10 minutes. Then, a solution of 1-[4-(2-bromoethyl)phenyl]-5-phenylpentan-1-ol (20.7 g) in methylene chloride (80 ml) was added thereto at −68 to −65° C. over 20 minutes and the mixture was stirred at the said temperature for an hour. Triethylamine (41.6 ml) was further added thereto over 10 minutes at the said temperature and the mixture was stirred for 2.5 hours while raising the temperature of the mixture to 0° C. gradually. The reaction mixture was washed with water (100 ml) and saturated brine (100 ml), dried over anhydrous sodium sulfate and the solvent was distilled away under reduced pressure to give a brown oily substance. The obtained brown oily substance was purified by silica gel column chromatography (eluent; hexane: ethyl acetate=20:1) to give 1-[4-(2-bromoethyl)phenyl]-5-phenylpentan-1-one (18.2 g) as a yellow oily substance.

$^1$H-NMR (270 MHz/CDCl$_3$) δ: 1.65–1.90 (4H, m), 2.67 (2H, t, J=7.3 Hz), 2.97 (2H, t, J=7.3 Hz), 3.22 (2H, t, J=7.3 Hz), 3.59 (2H, t, J=7.3 Hz), 7.15–7.20 (3H, m), 7.20–7.35 (4H, m), 7.90 (2H, d, J=7.9 Hz)

MS (EI) m/z 345(M$^+$)

(4) Synthesis of 1-[4-(2-iodoethyl)phenyl]-5-phenylpentan-1-one

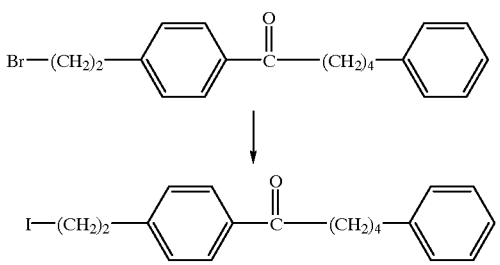

A solution of 1-[4-(2-bromoethyl)phenyl]-5-phenylpentan-1-one (18.2 g) and sodium iodide (9.5 g) in 2-butanone (180 ml) was stirred at 60° C. for 3.5 hours. The reaction mixture was poured into water and extracted with ethyl acetate. The organic layer was washed with saturated brine, dried over anhydrous sodium sulfate and the solvent was distilled away under reduced pressure to give a brown oily substance (19.2 g). The obtained brown oily substance was purified by silica gel column chromatography (eluent; hexane: ethyl acetate=20:1) to give 1-[4-(2-iodoethyl)phenyl]-5-phenylpentan-1-one (17.2 g) as a yellow oily substance.

$^1$H-NMR (270 MHz/CDCl$_3$) δ: 1.65–1.85 (4H, m), 2.67 (2H, t, J=7.3 Hz), 2.97 (2H, t, J=7.9 Hz), 3.23 (2H, m), 3.36 (2H, m), 7.10–7.20 (3H, m), 7.20–7.35 (4H, m), 7.90 (2H, d, J=8.6 Hz)

MS (EI) m/z 392(M$^+$)

IR (neat) cm$^{-1}$: 3025, 2935, 2858, 1684, 1571

(5) Synthesis of diethyl 2-acetamido-2-{2-[4-(1-oxo-5-phenylpentyl)phenyl]-ethyl}malonate

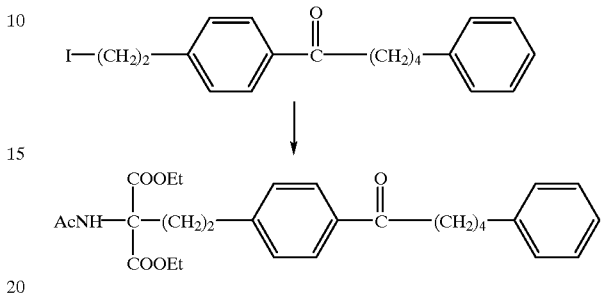

A solution of diethyl 2-acetamidomalonate (30.6 g), sodium ethoxide (7.6 g) and molecular sieves 3A (5.5 g) in ethanol (80 ml) was stirred at room temperature for 20 hours. A solution of 1-[4-(2-iodoethyl)phenyl]-5-phenylpentan-1-one (18.4 g) in tetrahydrofuran (60 ml) was added thereto over 10 minutes and the mixture was refluxed under heating for 15 hours. The reaction mixture was poured into water (200 ml) and extracted with ethyl acetate. The organic layer was washed with saturated brine, dried over anhydrous magnesium sulfate and the solvent was distilled away under reduced pressure to give a brown oily substance (40 g). The obtained brown oily substance was purified by silica gel column chromatography (eluent; hexane: ethyl acetate=2:1) to give diethyl 2-acetamido-2-{2-[4-(1-oxo-5-phenylpentyl)phenyl]ethyl}malonate (13.8 g) as a pale yellow oily substance.

$^1$H-NMR (270 MHz/CDCl$_3$) δ: 1.25 (6H, t, J=7.3 Hz), 1.65–1.85 (4H, m), 1.98 (3H, s), 2.50–2.60 (2H, m), 2.65–2.80 (4H, m), 2.90–3.00 (2H, m), 4.15–4.30 (4H, m), 6.78 (1H, s), 7.15–7.30 (7H, m), 7.84 (2H, d, J=8.6 Hz)

MS (EI) m/z 482 (M+1)$^+$IR (neat) cm$^{-1}$: 3381, 2981, 2937, 1739, 1681, 1606

(6) Synthesis of diethyl 2-acetamido-2-{2-[4-(1,1-ethylenedioxy-5phenylpentyl)phenyl]ethyl}malonate

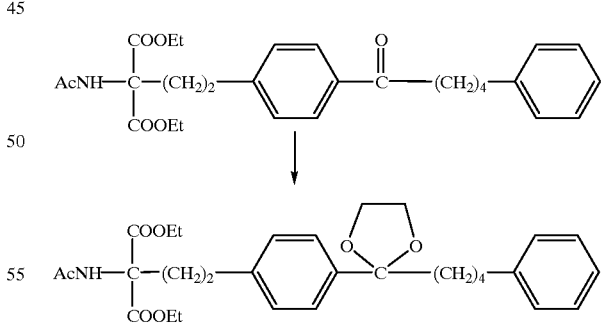

A solution of diethyl 2-acetamido-2-{2-[4-(1-oxo-5-phenylpentyl)phenyl]ethyl}malonate (13.5 g), ethylene glycol (3.1 ml) and p-toluenesulfonic acid (0.53 g) in benzene (135 ml) was refluxed under heating for 20 hours, while dehydrating with Dean-Stark trap. The reaction mixture was treated with triethylamine (2.4 ml) and ethyl acetate (200 ml) was added thereto. The mixture was washed with water and saturated brine, dried over anhydrous sodium sulfate and the solvent was distilled away under reduced pressure to give a pale yellow oily substance (15.9 g). The obtained pale yellow oily substance was purified by silica gel column chromatography (eluent; hexane: ethyl acetate=1:1) to give diethyl 2acetamido-2-{2-[4-(1,1-ethylenedioxy-5-phenylpentyl)phenyl]ethyl}malonate (14.1 g) as a colorless transparent oily substance.

$^1$H-NMR (270 MHz/CDCl$_3$) δ: 1.25 (6H, t, J=7.3 Hz), 1.30–1.45 (2H, m), 1.50–1.60 (2H, m), 1.85–1.95 (2H, m), 1.98 (3H, s), 2.45–2.60 (4H, m), 2.65–2.65 (2H, m), 3.70–3.75 (2H, m), 3.95–4.00 (2H, m), 4.15–4.30 (4H, m), 6.77 (1H, s), 7.05–7.25 (7H, m), 7.33 (2H, d, J=8.6 Hz)

MS (EI) m/z 525(M$^+$)

IR (neat) cm$^{-1}$: 3410, 2942, 1739, 1683, 1496

(7) Synthesis of 2-acetamido-2-{2-[4-(1,1-ethylenedioxy-5-phenylpentyl)phenyl]ethyl}propane-1,3-diol

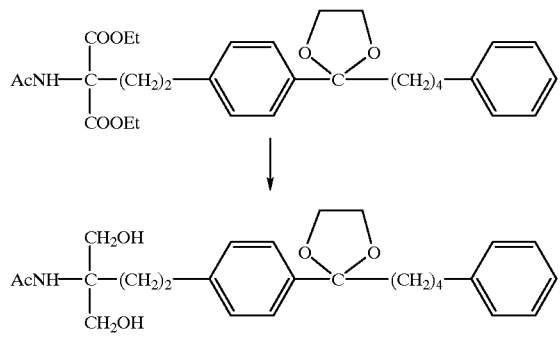

To a solution of lithium aluminum hydride (2.0 g) in tetrahydrofuran (100 ml) was dropwise added a solution of diethyl 2-acetamido-2-{2-[4-(1,1-ethylenedioxy-5-phenylpentyl)phenyl]ethyl}malonate (14.0 g) in tetrahydrofuran (50 ml) at 3–13° C. over 30 minutes, and the mixture was stirred at room temperature for 2 hours. To the reaction mixture was dropwise added a saturated aqueous sodium sulfate solution (27 ml), and the mixture was stirred at room temperature for an hour. The precipitate was filtered through celite and the filtrate was concentrated under reduced pressure to give a colorless transparent oily substance (11.7 g). The obtained colorless transparent oily substance was purified by silica gel column chromatography (eluent; chloroform:methanol=20:1) to give 2acetamido-2-{2-[4-(1,1-ethylenedioxy-5-phenylpentyl)phenyl]ethyl}propane-1,3-diol (5.8 g) as a colorless transparent oily substance.

$^1$H-NMR (270 MHz/CDCl$_3$) δ: 1.30–1.45 (2H, m), 1.50–1.65 (2H, m), 1.80–2.00 (4H, m), 1.96 (3H, s), 2.54 (2H, m), 2.64 (2H, m), 3.55–3.65 (2H, m), 3.70–3.80 (2H, m), 3.80–3.90 (2H, m), 3.954.05 (2H, m), 5.98 (1H, s), 7.05–7.25 (4H, m), 7.10–7.15 (3H, m), 7.20–7.25 (7H, m), 7.35 (2H, d, J=8.6 Hz)

MS (EI) m/z 441(M$^+$)

IR (neat) cm$^{-1}$: 3323, 2945, 1652

(8) Synthesis of 2-amino-2-{2-[4-(1-oxo-5-phenylpentyl)phenyl]ethyl}propane-1,3-diol

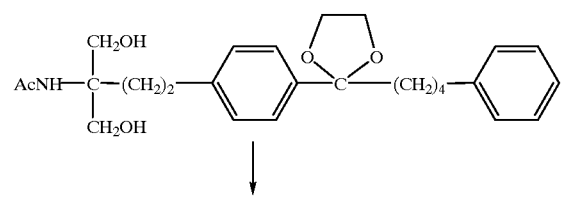

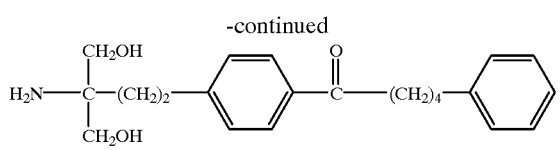

A solution of 2-acetamido-2-{2-[4-(1,1-ethylenedioxy-5phenylpentyl)phenyl]ethyl}propane-1,3-diol (5.5 g), concentrated hydrochloric acid (7 ml) and water (20 ml) in tetrahydrofuran (200 ml) was refluxed under heating for 7 hours. The mixture was adjusted to pH 12 with 1N sodium hydroxide and extracted with ethyl acetate. The organic layer was washed with saturated brine, dried over anhydrous sodium sulfate and the solvent was distilled away under reduced pressure to give a yellow solid (4.7 g). The obtained yellow solid was purified by silica gel column chromatography (eluent; chloroform: methanol=9:1) to give a white solid (3.76 g). The obtained white solid was crystallized from ethyl acetate and the obtained crystals were recrystallized from ethyl acetate-ethanol to give 2-amino-2-(2-(4-(1-oxo-5-phenylpentyl)phenyl)ethyl)propane-1,3-diol (2.34 g) as white crystals, melting point 126–127° C.

$^1$H-NMR (270 MHz/CDCl$_3$) δ: 1.60–1.80 (6H, m), 2.00 (4H, brs), 2.60–2.75 (4H, m), 2.95 (2H, t, J=7.2 Hz), 3.50–3.65 (4H, m), 7.10–7.15 (3H, m), 7.20–7.25 (4H, m), 7.86 (2H, d, J=7.9 Hz)

MS (EI) m/z 355(M$^+$)

IR (neat) cm$^{-1}$: 3349, 3290, 3025, 1678 elemental analysis: $C_{22}H_{29}NO_3$ calculated C, 74.33; H, 8.22; N, 3.94 found C, 74.35; H, 8.38; N, 3.86

WORKING EXAMPLE 3

Synthesis of 2-acetamido-1,3-diacetoxy-2-(2-(4-(1-oxo-5-phenylpentyl)phenyl)ethyl)propane 2-Acetamido-2-(2-(4-(1-oxo-5-phenylpentyl)phenyl) ethyl)propane-1,3diol is dissolved in pyridine, acetic anhydride is added thereto under ice-cooling and the mixture is allowed to stand at room temperature. The reaction mixture is poured into an aqueous hydrochloric acid solution and extracted with ethyl acetate. The organic layer is washed with an aqueous potassium hydrogencarbonate solution and saturated brine, dried over anhydrous magnesium sulfate and the solvent is distilled away. The residue is purified by silica gel column chromatography to give 2-acetamido-1,3-diacetoxy-2-(2-(4-(1-oxo-5-phenylpentyl)phenyl)ethyl) propane.

PREPARATION EXAMPLE 1

Synthesis of 2-amino-2-(2-(4-(1-oxo-6-phenylhexyl) phenyl)ethyl)propane-1,3-diol (1) Synthesis of 2-acetamido-1,3-bis(tert-butyldimethylsilyloxy)-2-(2-(4-(1hydroxy-6-phenylhexyl) phenyl)ethyl)propane

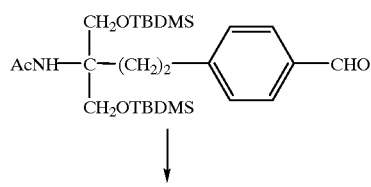

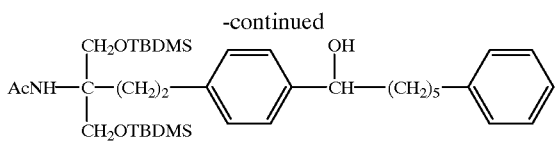

2-Acetamido-1,3-bis(tert-butyldimethylsilyloxy)-2-(2-(4-formylphenyl)ethyl)propane (3.0 g) and 1-bromo-5-phenylpentane (4.1 g) were reacted and treated in the same manner as in Working example 1(6) to give the title compound (2.7 g) as a pale yellow oily substance.

$^1$H-NMR (CDCl$_3$) δ: 0.06 (12H, s), 0.84 (18H, s), 1.20–1.80 (9H, m), 1.87 (3H, s), 2.04 (2H, m), 2.49–2.56 (4H, m), 3.61 (2H, d, J=9.2 Hz), 3.72 (2H, d, J=9.2 Hz), 4.54 (1H, t, J=6.6 Hz), 5.50 (1H, s), 7.07–7.11 (5H, m), 7.15–7.23 (4H, m) MS(EI): 584 ((M—AcNH)$^+$)

(2) Synthesis of 2-acetamido-1,3-bis(tert-butyldimethylsilyloxy)-2-(2-(4-(1oxo-6-phenylhexyl)phenyl)ethyl)propane

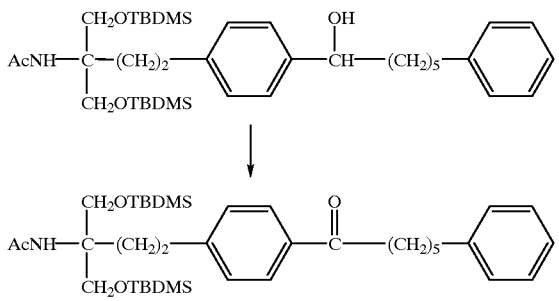

2-Acetamido-1,3-bis(tert-butyldimethylsilyloxy)-2-(2-(4-(1-hydroxy-6-phenylhexyl)phenyl)ethyl)propane (2.2 g) was reacted and treated in the same manner as in Working example 1(7) to give the title compound (2.1 g) as a pale yellow oily substance.

$^1$H-NMR (CDCl$_3$) δ: 0.06 (12H, s), 0.83 (18H, s), 1.35 (2H, m), 1.54–1.75 (4H, m), 1.89 (3H, s), 2.06 (2H, m), 2.53–2.62 (4H, m), 2.86 (2H, t, J=7.3 Hz), 3.60 (2H, d, J=9.2 Hz), 3.71 (2H, d, J=9.2 Hz), 5.52 (1H, s), 7.07–7.11 (3H, m), 7.12–7.23 (4H, m), 7.78 (2H, d, J=8.6 Hz)

IR(neat): 3311, 2952, 2929, 1683, 1657 cm$^{-1}$
MS(EI): 582 ((M—AcNH)$^+$)
elemental analysis: C$_{37}$H$_{61}$NO$_4$ Si$_2$.⅓H$_2$O calculated C; 68.96, H; 9.60, N; 2.17 found C; 68.99, H; 9.72, N; 2.20

(3) Synthesis of 2-amino-2-(2-(4-(1-oxo-6-phenylhexyl)phenyl)ethyl)propane-1,3-diol

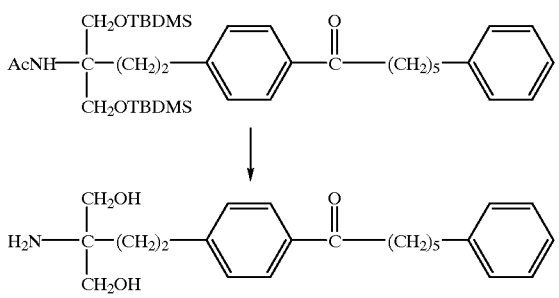

2-Acetamido-1,3-bis(tert-butyldimethylsilyloxy)-2-(2-(4-(1-oxo-6phenylhexyl)phenyl)ethyl)propane (2.0 g) was reacted and treated in the same manner as in Working example 1(8) to give the title compound (310 mg) as a white crystal substance, melting point 118–120° C.

$^1$H-NMR (CDCl$_3$) δ: 1.42 (2H, m), 1.61–1.81 (6H, m), 2.00–2.30 (4H, brs), 2.62 (2H, t, J=7.3 Hz), 2.70 (2H, m), 2.92 (2H, t, J=7.3 Hz), 3.52 (2H, d, J=10.6 Hz), 3.61 (2H, d, J=10.6 Hz), 7.14–7.18 (3H, m), 7.19–7.29 (4H, m), 7.86 (2H, d, J=8.6 Hz)

IR(KBr): 3352, 2933, 1676 cm$^{-1}$
MS(EI): 369 (M$^+$)
elemental analysis C$_{23}$H$_{31}$O$_3$.H$_2$O calculated C; 71.29, H; 8.58, N; 3.61 found C; 71.50, H; 8.32, N; 3.58

PREPARATION EXAMPLE 2

Synthesis of 2-amino-2-(4-(1-oxo-7-phenylheptyl)phenyl)ethyl)propane-1,3-diol (1) Synthesis of 2-acetamido-1,3-bis(tert-butyldimethylsilyloxy)-2-(2-(4-(1-hydroxy-7-phenylheptyl)phenyl)ethyl)propane

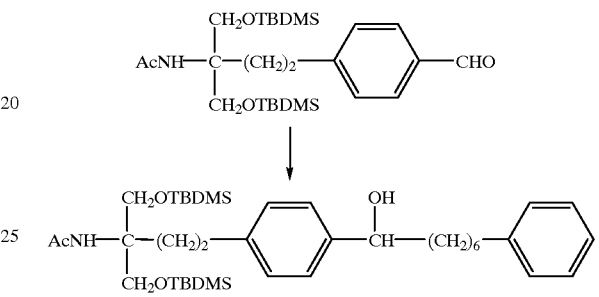

2-Acetamido-1,3-bis(tert-butyldimethylsilyloxy)-2-(2-(4-formylphenyl)ethyl)propane (3.0 g) and 1-bromo-6-phenylhexane (3.1 g) were reacted and treated in the same manner as in Working example 1(6) to give the title compound (2.6 g) as a pale yellow oily substance.

$^1$H-NMR (CDCl$_3$) δ: 0.06 (12H, s), 0.84 (18H, s), 1.20–2.10 (16H, m), 2.45–2.55 (4H, m), 3.64 (2H, d, J=9.2 Hz), 3.72 (2H, d, J=9.2 Hz), 4.55 (2H, t, J=6.6 Hz), 5.50 (1H, s), 7.05–7.20 (9H, m)

IR(neat): 3304, 3086, 3026, 2929, 1741 cm$^{-1}$
MS(EI): 656 (M$^+$)

(2) Synthesis of 2-acetamido-1,3-bis(tert-butyldimethylsilyloxy)-2-(2-(4-(1-oxo-7-phenylheptyl)phenyl)ethyl)propane

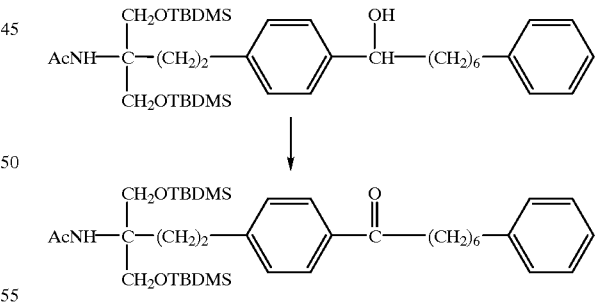

2-Acetamido-1,3-bis(tert-butyldimethylsilyloxy)-2-(2-(4-(1-hydroxy-7phenylheptyl)phenyl)ethyl)propane (2.2 g) was reacted and treated in the same manner as in Working example 1(7) to give the title compound (1.8 g) as a colorless transparent oily substance.

$^1$H-NMR (CDCl$_3$) δ: 0.06 (12H, s), 0.84 (18H, s), 1.25–1.35 (4H, m), 1.50–1.75 (4H, m), 1.89 (3H, s), 2.07 (2H, m), 2.50–2.65 (4H, m), 2.85 (2H, t, J=7.3 Hz), 3.60 (2H, d, J=9.2 Hz), 3.71 (2H, d, J=9.2 Hz), 5.52 (1H, s), 7.05–7.15 (3H, m), 7.18–7.24 (4H, m), 7.79 (2H, d, J=7.9 Hz)

IR(neat): 3313, 2929, 2856, 1684, 1606 cm$^{-1}$
MS(EI): 596 ((M—AcNH)$^+$)
elemental analysis: $C_{38}H_{63}NO_4$ $Si_2 \cdot 1/3H_2O$ calculated C; 69.40, H; 9.72, N; 2.13 found C; 69.12, H; 9.65, N; 2.02
(3) Synthesis of 2-amino-2-(2-(4-(1-oxo-7-phenylheptyl)phenyl)ethyl)propane-1,3-diol

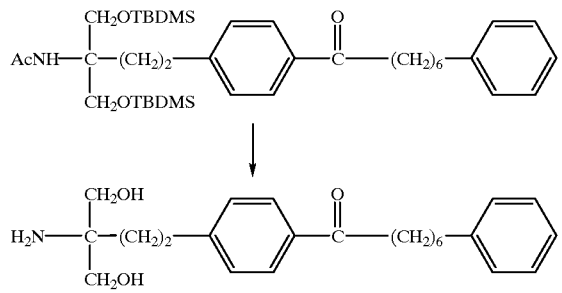

2-Acetamido-1,3-bis(tert-butyldimethylsilyloxy)-2-(2-(4-(1-oxo-7phenylheptyl)phenyl)ethyl)propane (1.8 g) was reacted and treated in the same manner as in Working example 1(8) to give the title compound (390 mg) as a white crystal substance, melting point 121–122° C.
$^1$H-NMR (CDCl$_3$) B: 1.30–1.45 (4H, m), 1.55–1.75 (6H, m), 2.00–2.20 (4H, brs), 2.60 (2H, t, J=7.9 Hz), 2.71 (2H, m), 3.52 (2H, d, J=10.6 Hz), 3.61 (2H, d, J=10.6 Hz), 7.13–7.20 (3H, m), 7.20–7.30 (4H, m), 7.86 (2H, d, J=8.6 Hz)
IR(KBr): 3288, 2929, 2854, 1676 cm$^{-1}$
MS(EI): 383 (M$^+$)
elemental analysis : $C_{24}H_{33}NO_3 \cdot 1/3H_2O$ calculated C; 74.46, H; 8.70, N; 3.62 found C; 74.54, H; 8.77, N; 3.58

FORMULATION EXAMPLE (1) Tablets

A tablet containing a compound of the present invention and having the following formulation is produced.

| Compound (I) | 1 mg |
|---|---|
| Lactose | 90 mg |
| Crystalline cellulose | 25 mg |
| Magnesium stearate | 4 mg |

(2) Soft capsules (per capsule)

| Compound (I) | 30 mg |
|---|---|
| Polyethylene glycol-300 | 300 mg |
| Polysorbate 80 | 20 mg |

Production method

Polyethylene glycol-300 and polysorbate 80 are added to a compound of the present invention and the mixture is packed in a soft capsule.

(3) Injections (per 10 ml in an ampoule)

| Compound (I) | 0.3% |
|---|---|
| Polyethylene glycol-300 | 20% |
| Ethanol | 60% |
| Injectable distilled water | amount to make the total 10 ml |

Production method

Ethanol and polyethylene glycol-300 are added to a compound of the present invention and injectable distilled water is added to reach the total volume.

Injections containing 30 mg of the compound of the present invention in an ampoule (10 ml) are thus obtained.

(4) 5% Ointment

| Compound of the present invention | 1 g |
|---|---|
| Hydrophilic petrolatum | 19 g |

Production method

A compound of the present invention (1 g) is dissolved in 19 g of hydrophilic petrolatum under heating at 60° C., and the mixture is cooled with stirring to prepare an ointment containing 5% of the compound of the present invention.

(5) 5% Ointment

| Compound of the present invention | 1 g |
|---|---|
| Plastibase | 19 g |

Production method

A compound of the present invention (1 g) is mixed well with 19 g of plastibase (hydrocarbon gel) in a mortar for 30 minutes to prepare an ointment containing 5% of the compound of the present invention.

(6) Suppository

| Compound of the present invention | 30 mg |
|---|---|
| Witepsol H15 | 72.47 g |

Production method

Witepsol H15 (72.47 g) is melted at 40° C. and a compound of the present invention (30 mg) is added. The mixture is stirred to disperse the compound. The homogeneous mixture is filled in a container at a weight of 725 mg each to prepare a suppository containing 0.3 mg of the compound of the present invention in 725 mg of the suppository.

(7) Eye drop

| Compound of the present invention | 0.2 g |
|---|---|
| Polyvinyl alcohol | 0.2 g |
| Polyoxyethylene hydrogenated castor oil 60 | 0.1 g |
| Disodium hydrogen phosphate | 0.5 g |
| Sodium dihydrogen phosphate | 0.1 g |
| Sodium chloride | 0.8 g |
| Benzethonium chloride | 0.007 g |
| Sterile purified water | amount to make the total 100 ml |

Production method

To 70 ml of sterile purified water is added 0.2 g of polyvinyl alcohol and the mixture is dissolved by heating at 70° C. with stirring. In the solution is dispersed homogeneously 0.1 g of polyoxyethylene hydrogenated castor oil 60, and then the mixture is cooled to room temperature. In this solution are dissolved 0.2 g of a compound of the present invention, 0.5 g of disodium hydrogen phosphate, 0.1 g of sodium dihydrogen phosphate, 0.8 g of sodium chloride and 0.007 g of benzethonium chloride. To the solution is added sterile purified water to make the total volume 100 ml to prepare an eye drop containing the compound of the present invention.

(8) Nasal drop

| | |
|---|---|
| Compound of the present invention | 0.4 g |
| Sodium citrate | 0.2 g |
| Polysorbate 80 | 0.1 g |
| Glycerin | 2.6 g |
| Benzethonium chloride | 0.007 g |
| Sterile purified water | amount to make the total 100 ml |

Production method

In 70 ml of sterile purified water are dissolved 0.4 g of a compound of the present invention, 0.2 g of sodium citrate, 0.1 g of polysorbate 80, 2.6 g of glycerin and 0.007 g of benzethonium chloride. To the solution obtained is added sterile purified water to make the total volume 100 ml to prepare a nasal drop containing the compound of the present.

(9) 2% Lotion

| | |
|---|---|
| Compound of the present invention | 100 mg |
| Isopropyl myristate | 1 ml |
| Ethanol | 4 ml |

Production method

To 100 mg of a compound of the present invention are added 1 ml of isopropyl myristate and 4 ml of ethanol to dissolve the compound at room temperature to prepare a lotion containing 2% of the compound of the present invention.

The action and effect of the present invention are explained in detail by illustrating experimental examples in the following.

For determining the immunosuppressive activity, various immune reactions can be measured using lymphocytes of mouse, rat or human. The immunosuppressive activity may be determined with high sensitivity, for example, by an allogenic mixed lymphocyte reaction (allogenic MLR) of mouse, rat or human.

The allogenic MLR is a blastogenesis of lymphocytes induced by a mixed culture of lymphocytes such as spleen cells, lymph node cells and peripheral blood lymphocytes, derived from two individuals, which are allogenic and have different major histocompatibility antigens. The allogenic MLR is a phenomenon induced by and reflects the difference in major histocompatibility antigens of the donors of the lymphocytes, and a blastogenesis phenomenon of the lymphocytes is not developed by a mixed culture of the lymphocytes from monozygotic twins. Accordingly, allogenic MLR is widely used for the donor-recipient selection in organ transplantations.

When allogenic MLR is desired, one way-MLR, wherein the lymphocytes of one of them are used as stimulator cells upon X-ray irradiation or treatment with mitomycin C to inhibit proliferation and when the blastogenesis of lymphocytes of the other (responder cells) is determined, may be carried out.

Further, the immunosuppressive activity can be determined as an activity to inhibit induction of cytotoxic T cells having the major histocompatibility antigen restrictive property during allogenic MLR.

Also, the immunosuppressive activity can be determined, besides allogenic MLR, as an activity to inhibit the blastogenesis of the lymphocytes induced by the stimulation of various mitogens such as concanavalin A, phytohemagglutinin and pokeweed mitogen or as an activity to inhibit the proliferation of the lymphocytes induced by a cytokine (e.g. interleukin 1, 2, 3, 4, 5 or 6) having an activity to reinforce the proliferation or promote the differentiation of the lymphocytes such as T cells or B cells, or manifestation of such function. In addition, it is possible to evaluate the immunosuppressive activity according to the inhibition of the production of these cytokines from T cells or macrophages.

Alternatively, the activity can be evaluated as an activity to inhibit induction of allogenic cell-specific cytotoxic T cells induced in spleen cells of mouse previously immunized with, for example, allogenic cells by intraperitoneally, orally, intravenously, intradermally, subcutaneously or intramuscularly administering a compound to mice; as an activity to inhibit the production of an allogenic cell-specific antibody produced in the blood serum of mouse immunized with allogenic cells or the like. The activity can be also evaluated as an activity to inhibit rejection of organ transplantation among allogenic skin, heart, liver, kidney and so on, or graft-versus-host reaction (GvHR) and host-versus-graft reaction (HvGR) by administering a compound to rat, dog or the like. Moreover, the activity can be evaluated as an activity to inhibit delayed hypersensitivity reaction, adjuvant arthritis, experimental allergy encephalomyelitis, experimental autoimmune uveitis or the like by administering a compound to mouse, rat or the like.

Moreover, the immunosuppressive activity may be evaluated as an activity to inhibit, for example, production of anti-DNA antibodies, production of rheumatoid factors, nephritis, abnormal proliferation of lymphocytes or urinary protein; or a macrobiotic effect by the administration of the compound to MRL/lpr mice, NZB/WF$_1$ mice, BXSB mice, NOD mice and the like which are spontaneous model animals with autoimmune diseases.

EXPERIMENTAL EXAMPLE 1

(Inhibition of allogenic mixed lymphocyte reaction in rat)

The rat allogenic mixed lymphocyte reaction (hereinafter referred to as rat allogenic MLR) is carried out by a mixed culture of nylon wool nonadhesive spleen cells from F344 rat as responder cells and spleen cells from WKAH rat treated with mitomycin C as stimulator cells that are used at the same ratio.

The responder cells are prepared as follows. A spleen is removed from a 4- to 10-week-old F344 rat and a single cell suspension of spleen cells is obtained by the use of RPMI1640 medium (containing kanamycin sulfate 60 μg/ml, penicillin G potassium 100 units/ml, N-2-hydroxyethyl-piperazine-N'2-ethanesulfonate 10 mM, 0.1% sodium hydrogencarbonate and L-glutamine 2 mM) supplemented with 5% heat-inactivated fetal calf serum (hereinafter referred to as FCS). After hemolysis treatment, the spleen cells are passed through a nylon wool column and non-adhesive cells are collected. The nylon non-adhesive cells are adjusted to a concentration of $10^7$ cells/ml by the use of RPMI1640 medium containing $10^{-4}$ M 2-mercaptoethanol and 10% FCS and used as a responder cell suspension.

The stimulator cells are prepared as follows. A spleen is removed from a 4- to 10-week-old WKAH rat and a single cell suspension of spleen cell is obtained by the use of RPMI1640 medium. After hemolysis treatment, the suspension is treated with 40 μg/ml mitomycin C at 37° C. for 60 minutes. After washing three times, the suspension is adjusted to a concentration of $10^7$ cells/ml by the use of RPMI1640 medium containing $10^{-4}$ M 2mercaptoethanol and 10% FCS and used as a stimulator cell suspension.

The responder cell suspension (50 μl) prepared by the method described above, the stimulator cell suspension (50

μl) prepared by the method described above and a test sample (100 μl) prepared by the use of RPMI1640 medium containing 10% FCS are placed in a 96 well flat-bottomed micro test plate and cultured at 37° C. under 5% $CO_2$—95% air for 4 days.

The blastogenesis reaction of lymphocytes in rat allogenic MLR is determined by a method using $^3$H-thymidine uptake as an index. Namely, after the culture, $^3$H-thymidine 18.5 KBq/well is added and the cells are cultured for 4 hours. The cells are collected by a cell harvester and the radioactivity incorporated into the cells is determined by a liquid scintillation counter and used as an index for the lymphocyte blastogenesis in rat allogenic MLR. The inhibition of rat allogenic MLR is calculated by the formula below and evaluated accordingly.

$$\text{Inhibition} (\%) = \left[1 - \frac{\left(\begin{array}{c}\text{cpm of MLR}\\ \text{with test sample}\end{array}\right) - \left(\begin{array}{c}\text{cpm of responder}\\ \text{cells alone}\end{array}\right)}{\left(\begin{array}{c}\text{cpm of MLR}\\ \text{without test sample}\end{array}\right) - \left(\begin{array}{c}\text{cpm of responder}\\ \text{cells alone}\end{array}\right)}\right] \times 100$$

The compounds of the present invention show an $IC_{50}$ value (a concentration to inhibit by 50%) of from about 1 nM to about 50 nM in a rat allogenic mixed lymphocyte reaction.

EXPERIMENTAL EXAMPLE 2

(Inhibition of proliferation of interleukin 2 (IL-2)-dependent mouse T cell line CTLL-2 induced by IL-2)

An IL-2-dependent mouse T cell line CTLL-2 is prepared to a concentration of $2 \times 10^5$ cells/ml in RPMI1640 medium containing 10% FCS. A cell suspension thereof (50 μl), recombinant human IL-2 (rh-IL-2) 40 U/ml (50 μl) and a test sample (100 μl) prepared by the use of RPMI1640 medium containing 10% FCS are placed in a 96 well flat-bottomed micro test plate and cultured at 37° C. under 5% $CO_2$—95% air for 68 hours. After the culture, 100 μl of the supernatant of each well is removed and a 5 mg/ml MTT [3-(4,5-dimethylthiazol-2-yl)-2,5-diphenyltetrazolium bromide] solution is added to each well by 20 μl and the cells are incubated at 37° C. for 4 hours. Then, 0.01N hydrochloric acid solution (100 μl) containing 10% sodium dodecyl sulfate is added thereto and the cells are incubated at 37° C. overnight. The purple formazan crystals produced are dissolved and the absorbance at 570 nm is measured using a microplate absorbance photometer and used as an index of the proliferation of the IL-2-dependent CTLL-2 cells. The inhibition (%) of the IL-2-dependent proliferation is calculated by the following formula.

$$\text{Inhibition} (\%) = \left[1 - \frac{\left(\begin{array}{c}\text{absorbance when}\\ \text{test sample and}\\ \text{rh-IL-2 are added}\end{array}\right) - \left(\begin{array}{c}\text{absorbance when}\\ \text{rh-IL-2 is not added}\end{array}\right)}{\left(\begin{array}{c}\text{absorbance when}\\ \text{rh-IL-2 alone}\\ \text{is added}\end{array}\right) - \left(\begin{array}{c}\text{absorbance when}\\ \text{rh-IL-2 is not added}\end{array}\right)}\right] \times 100$$

The compounds of the present invention show an $IC_{50}$ value (a concentration to inhibit by 50%) of from about 1 nM to about 50 nM in the IL-2-dependent proliferation of mouse T cell line CTLL-2.

EXPERIMENTAL EXAMPLE 3

(Inhibitory effect on delayed type hypersensitivity reaction in mice)

BALB/c mice at 5 weeks of age are sensitized by subcutaneous injection to the back with 0.1 ml of 0.25% methylated human serum albumin (MeHSA) solution. Four days after sensitization, the volume of right hind foot in mice is measured using foot volume measuring apparatus (TK-102; Neuroscience Co., Ltd.) and thereafter 25 μl of 0.25% MeHSA solution is injected into the right hind foot pad in order to induce delayed hypersensitivity reaction (DTH reaction). After 24 hours from the injection, namely after 5 days from sensitization, the volume of right hind foot is measured again. The test compounds are examined by the differences of the foot volumes between at 5 days and 4 days, namely the swelling in the volume of right hind foot pad as an indicator of DTH reaction. At this time, the body weight, wet weight of thymus and spleen and the number of peripheral white blood cells are also measured. Test compounds are administered orally for 5 consecutive days from the day of sensitization.

The compounds of the present invention show statistically significant inhibitory effect on DTH reaction by administration at 0.1 to 10 mg/kg.

EXPERIMENTAL EXAMPLE 4

(Inhibitory effect on host versus graft reaction in rats)

A spleen is removed from a male WKAH rat at 4 to 5 weeks of age and is used to obtain a single cell suspension of spleen cells using RPMI1640 medium (containing kanamycin sulfate at 60 μg/ml, penicillin G potassium at 100 units/ml, N-2-hydroxyethylpiperazine-N'-2ethanesulfate at 10 mM, 0.1% sodium bicarbonate and L-glutamine at 2 mM). After hemolysis treatment, the cells are washed three times with RPMI1640 medium and are adjusted at $5 \times 10^7$ cells/ml with physiological saline for injection. By injection of 100 μl of the spleen cell suspension into right hind foot pad of male LEW rats at 4–5 weeks of age, the host versus graft reaction (HvG reaction) is induced. After 4 days of the injection of the cells, both of right and left popliteal lymph nodes are removed and the weight of them is measured. The test compounds are examined by difference between the right popliteal lymph node weight and the left popliteal lymph node weight as an indicator of HvG reaction. In addition, after 4 days from the injection of the cells, blood is obtained from tail vein of the rats and the number of peripheral white blood cells is measured using automatic hemocytometer for animal (MEK-5158, Nihonkouden Co., Ltd.). Test compounds are intravenously or orally administered daily for 4 days after the injection of the cells.

EXPERIMENTAL EXAMPLE 5

(Inhibitory effect on graft versus host reaction in rats)

There are two types of graft versus host reactions (GvH reaction) which are systemic and local GvH reactions. Systemic GvH reaction is induced by intravenous administration of cyclophosphamide at 150 ml/kg to 5-week-old female (LEW×BN)$F_1$ rats and by intravenous injection of $5 \times 10^7$ spleen cells from female LEW rats at 5 weeks of age to them on the next day. Test compounds are examined by determining the survival time after the induction of systemic GvH reaction. Local GvH reaction is induced by subcutaneous injection of $2 \times 10^7$ spleen cells from 5-week-old male LEW rats into the right hind foot pad of female (LEW×BN) $F_1$ rats at 5 weeks of age and after 7 days, popliteal lymph nodes are removed and their weights are measured. Test compounds are orally administered daily for 30 days and 7 days from the day of cell injection in the case of systemic reaction and local GvH reaction, respectively.

EXPERIMENTAL EXAMPLE 6
(Inhibitory effect on antibody production against sheep red blood cells in rats)

Four to six-week-old male F344 rats are immunized by intravenous injection with $1 \times 10^8$ of sheep red blood cells. After 4 days from immunization, the spleen is removed, and the number of anti-sheep red blood cell antibody producing cells are counted by direct hemolytic plaque forming assay using sheep red blood cells and guinea pig complement. In this case, the body weights, wet weights of thymus and spleen, and the number of spleen cells are also measured. Test compounds are orally administered daily for 4 days after the day of immunization.

EXPERIMENTAL EXAMPLE 7
(Inhibitory effect on adjuvant arthritis in rat)

Dead tuberculosis bacterium (R35H5v-1 strain, 0.5 mg) is suspended as an adjuvant in 0.1 ml of liquid paraffin and inoculated to the root of tail of an 8-week-old male LEW rat. After the inoculation up to day 21 of the adjuvant, the presence or absence or the onset of arthritis is observed and the day of onset of arthritis and the ratio of the onset cases are determined. The swelling of right hind foot pad of the rat is periodically measured by using foot volume measuring apparatus (TK-102; Neuroscience Co., Ltd.). At day 21, the roentgenogram of the hind foot of the rats is taken, based on which the degree of destruction of articulation is evaluated. Test compounds are orally or intravenously administrated from the day of adjuvant inoculation daily for 21 days.

When the test compound is not administered, arthritis is found in all 7 rats inoculated with adjuvant at day 9.6±0.5, along with swelling of hind limbs and destruction of the articulation.

The compounds of the present invention delayed the onset of and decreased the ratio of the onset cases of the adjuvant arthritis to a statistically significant degree and significantly suppressed swelling of the hind limbs and destruction of the articulation by the administration of 0.1–10 mg/kg thereof.

EXPERIMENTAL EXAMPLE 8
(Inhibitory effect on collagen-induced arthritis in rats)

Seven to eight-week-old male Sprague-Dawley rats are intracutaneously injected by division of 5 portions with 1 ml of emulsion which are prepared by mixing 0.1 N acetic acid solution containing bovine type II collagen at 2 mg/ml with Freund's incomplete adjuvant at a volume ratio of 1:1. After 7 days, re-immunization is performed by intracutaneous injection of collagen emulsion prepared by the same method into the root of tail. The swelling of right hind foot pad of the rat is periodically measured by using foot volume measuring apparatus (TK-102; Neuroscience Co., Ltd.).

Additionally, after 10 and 21 days from primary immunization with collagen, the blood is collected and anti-type II collagen antibody titer of the serum is measured by ELISA method. Test compounds are orally or intravenously administered daily for 21 days from the day of primary immunization.

EXPERIMENTAL EXAMPLE 9
(Inhibitory effect on experimental allergic encephalomyelitis in rats)

Eight-week-old female LEW rats are immunized by intracutaneous injection to their right hind foot pad with 0.1 ml of emulsion of Freund's complete adjuvant containing 100 μg of myelin basic protein (MBP) purified from spinal cord of guinea pigs and 100 μg of dead Mycobacterium tuberculosis H37 RA. Thereafter somatic symptoms after immunization are judged according to the standards of 6 levels.

Score 0: No symptoms
Score 1: Weakness of tail
Score 2: Weakness of hind limbs
Score 3: Paralysis of only one hind limb
Score 4: Paralysis of both hind limbs
Score 5: Incontinence of urine or death Additionally, after 20 days from immunization with MBP, the spinal cords are removed from the rats to make tissue section and the histology of them are investigated after staining by hematoxylin-eosin method. Test compounds are orally administered daily for 20 days after the day of immunization.

EXPERIMENTAL EXAMPLE 10
(Inhibitory effect on experimental autoimmune uveitis)

Eight-week-old female LEW rats are immunized by intracutaneous injection to their right hind foot pad with 0.1 ml of emulsion of Freund's complete adjuvant containing 30 μg of soluble antigen (s-antigen) purified from bovine retina and 100 μg of dead Mycobacterium tuberculosis H37 RA. Onset and seriousness of uveitis are periodically inspected after the immunization. Seriousness of uveitis is judged according to the following standards.

Score 0: No inflammation
Score 1: Weak, or light (hyperemia of iris and emergence of exudate in arterior chamber)
Score 2: Medium (small hypopyon)
Score 3: Strong (noticeable hypopyon and exophthalmos)

Additionally, after 15 days from immunization with s-antigen, eyeballs are removed from the rats to make tissue section and the histology of them is investigated after staining by hematoxylin-eosin method.

Score 0: No infiltration of inflammation-associated cells
Score 1: Slight infiltration
Score 2: Weak or light infiltration
Score 3: Medium infiltration and partial destruction of visual cell layer
Score 4: Remarkable infiltration and complete destruction of visual cell layer Test compounds are orally administered daily for 15 days after the day of immunization.

EXPERIMENTAL EXAMPLE 11
(Effect on survival of MRL/lpr mice as a model of spontaneous systemic lupus erythematosus)

Test compounds are orally administered to male MRL/lpr mice. For the assessment of prophylactic effect, daily administration is continued until 8 to 45 weeks of age and for the assessment of therapeutic effect, until 16 to 20 weeks of age. Mortality during the administration period is recorded and blood and urine periodically obtained from the animals are measured for the titers of anti-nuclear antibodies and rheumatoid factor in the serum, and protein in the urine.

EXPERIMENTAL EXAMPLE 12 (Prolonging effect of skin graft on allogenic skin graft in rats)

A full-thickness skin graft (1.5×1.5 cm) of a 4-week-old male WKAH rat or LEW rat is grafted to a graft bed on the back of a 4-week-old male F344 rat by suture. The graft is covered with a sterile gauze and bound. The bandage is removed 5 days after the grafting and the skin graft is observed daily until it is rejected. The skin graft is considered to be rejected when 90% or more of the epithelium of the skin graft showed necrosis and turned brown. The number of days from the grafting to rejection is taken as a graft survival days. Test compounds are intraperitoneally, intravenously or orally administered repeatedly once a day for 14 days.

In the control group administered with vehicle alone, mean survival time for grafting the skin of a WKAH rat to an F344 rat was 7.0±0.0 days. The results obtained by oral administration of Compound (I-a) of the present invention at a dose of 1 mg/kg or 10 mg/kg are shown in FIG. 1. The comparative compound 1 was 2-amino-2-(2-(4-(4-phenylbutyloxy)phenyl)ethyl)propane-1,3-diol disclosed in WO94/08943, comparative compound 2 was 2-amino-2-methyl-2-(2-(4-(4-phenylbutyloxy)phenyl)butanol disclosed in WO96/06068.

As shown in FIG. 1, mean survival time of the group administered with the compound of the present invention upon grafting of the skin of a WKAH rat to an F344 rat was 16.6∓1.2 days, and the mean survival time of comparative compound 1 and comparative compound 2 were 11.9±0.7 days and 15.6±1.4 days, respectively. The compound of the present invention prolonged graft survival days statistically significantly as compared to the control group and comparative compound 1 group. It showed an equivalent prolonging effect with comparative compound 2.

The mean survival time upon grafting of the skin of an LEW rat to an F344 rat was 8.2±0.4 days, whereas that upon administration of Compound (I-a) of the present invention was 20 days or more, thus showing a statistically significant prolonging effect as compared to the control group administered with vehicle alone.

EXPERIMENTAL EXAMPLE 13
(Body weight change on allogenic skin graft in rats)

Figure 2:
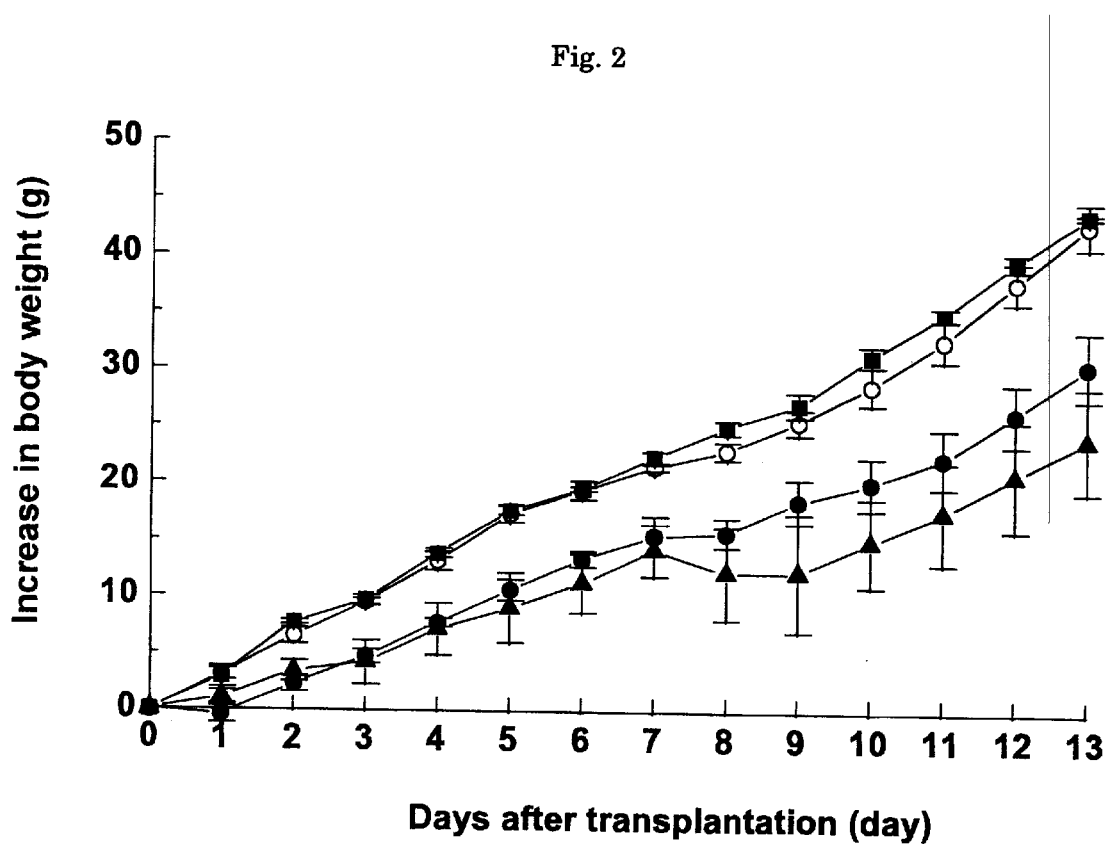
FIG. 2 is a graph which shows the results of Experimental Example 13, wherein —●— shows the result of control, —○— shows the result of comparative compound 1 (10 mg/kg), —△— shows the result of comparative compound 2 (10 mg/kg) and —■— shows the result of Compound (I-a) of the present invention (10 mg/kg).

The changes in body weight in rats of Experimental Example 12 on testing of allogenic skin graft in rats, after 13 days of consecutive repeat oral administration of 10 mg/kg of test compounds are shown in FIG. 2.

As shown in FIG. 2, the group administered with the compound of the present invention showed natural gain of body weight as in the control group, whereas the group administered with comparative compound 1 and the group administered with comparative compound 2 showed a suppressive effect on the gain of the body weight, which is attributable to disorders of gastrointestinal organ and therewith associated decrease in food intake. As a result, there is a risk of serious side effects such as nutrition intake disorder due to increase of dose and long term consecutive administration, and further, fatal consequences. In contrast, the group administered with the compound of the present invention showed a similar increase in body weight as the control group, which indicates that the compound of the present invention is a highly safe immunosuppressant with less toxicity, which is free of the aforementioned side effects.

EXPERIMENTAL EXAMPLE 14
(Prolonging effect on graft survival of cardiac graft on allogenic cardiac graft in rats)

The hearts from the male WKAH rats at 10 to 14 weeks of age are heterotopically transplanted in subcutaneous locations at cervixes of male ACI/N rats at 10 to 14 weeks of age using vascular anastomosis. The transplanted hearts are judged to be rejected in the case of the cessation of heart beat, then survival time was calculated. Test compounds are orally administered repeatedly for 15 days from the day of transplantation.

EXPERIMENTAL EXAMPLE 15
(Prolonging effect on graft survival of renal graft on allogenic renal graft in dogs)

Mongrel and beagle dogs are used as donors and recipients, respectively, and then the prolonging effect on the survival of transplanted kidney is examined by performing surgery of renal transplantation. After the transplantation, the blood was collected from the transplanted animals periodically to measure the levels of serum creatinine and blood urea nitrogen (BUN).

EXPERIMENTAL EXAMPLE 16
(Inhibition of blastogenesis reaction of rat spleen cells induced by stimulation with concanavalin A)

Inhibition effects of blastogenesis reaction of rat spleen cells induced by stimulation with concanavalin A is tested in the following manner.

A spleen is removed from a 4- to 10-week-old male F344 rat. The removed spleen is opened with scissors and filtered through RPMI1640 medium supplemented with 10%FCS using a stainless mesh to give a single cell suspension of spleen cells. After hemolysis treatment, the spleen cells are passed through a nylon wool column and non-adhesive cells are collected. The collected nylon non-adhesive cells ($5\times10^6$ cells/ml) are cultured in RPMI1640 medium containing 5 μg/ml concanavalin A, $5\times10^{-5}$ M 2-mercaptoethanol and 10% FCS at 37° C. under 5% $CO_2$—95% air for 72 hours. $^3$H-thymidine 18.5 KBq/well is added and the cells are cultured for 4 hours. The cells are collected by a cell harvester and the radioactivity incorporated into the cells is determined by a liquid scintillation counter and used as an index for the blastogenesis of rat spleen cells.

The compounds of the present invention show an $IC_{50}$ value (a concentration to inhibit by 50%) of from about 1 nM to about 50 nM in blastogenesis reaction of rat spleen cells induced by stimulation with concanavalin A.

INDUSTRIAL APPLICABILITY

From various pharmacological testings inclusive of the abovementioned Experimental Examples and toxicity testing, it is evident that Compound (I) of the present invention, a pharmaceutically acceptable acid addition salt thereof and a hydrate thereof show superior immunosuppressive action without inhibitory action on body weight increase which is related to serious side effects, and are useful as superior immunosuppressants with less toxicity and higher safety. Moreover, the Compound (II) and Compound A of the present invention are useful as synthetic intermediates for Compound (I) which is useful as an immunosuppressant.

The present application is based on Patent Application No. 86255/1997 filed in Japan, the content of which is incorporated hereinto by reference.

What is claimed is:

1. A 2-aminopropane-1,3-diol compound of the general formula

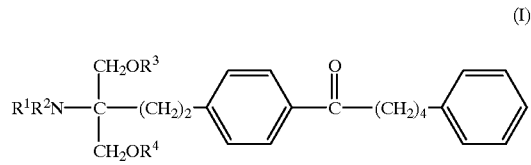

(I)

wherein $R^1$, $R^2$, $R^3$ and $R^4$ are the same or different and each is a hydrogen or an acyl; a pharmaceutically acceptable acid addition salt thereof or a hydrate thereof.

2. The 2-aminopropane-1,3-diol compound according to claim 1, which is 2-amino-2-(2-(4-(1-oxo-5-phenylpentyl)phenyl)ethyl)propane-1,3-diol, a pharmaceutically acceptable acid addition salt thereof or a hydrate thereof.

3. A pharmaceutical comprising the 2-aminopropane-1,3-diol compound according to claim 1, a pharmaceutically acceptable acid addition salt thereof or a hydrate thereof.

4. An immunosuppressant comprising, as an active ingredient, the 2-aminopropane-1,3-diol compound according to claim 1, a pharmaceutically acceptable acid addition salt thereof or a hydrate thereof.

5. A suppressant of rejection comprising, as an active ingredient, the 2-aminopropane-1,3-diol compound according to claim 1, a pharmaceutically acceptable acid addition salt thereof or a hydrate thereof.

6. An agent for the treatment of graft-versus-host diseases comprising, as an active ingredient, the 2-aminopropane-1,3-diol compound according to claim 1, a pharmaceutically acceptable acid addition salt thereof or a hydrate thereof.

7. An agent for the treatment of autoimmune diseases or allergic diseases comprising, as an active ingredient, the 2-aminopropane-1,3-diol compound according to claim 1, a pharmaceutically acceptable acid addition salt thereof or a hydrate thereof.

8. A pharmaceutical composition comprising the 2-aminopropane-1,3-diol compound according to claim 1, a pharmaceutically acceptable acid addition salt thereof or a hydrate thereof, and a pharmaceutically acceptable carrier.

9. 2-Amino-2-(2-(4-(1-hydroxy-5-phenylpentyl)phenyl)ethyl)propane-1,3-diol, a compound thereof wherein at least one of the amino group and the hydroxy group is protected, or a salt thereof.

10. (Amended) 2-Amino-2-(2-(4-formylphenyl)ethyl)propane-1,3-diol, a compound thereof wherein at least one of the amino group and the hydroxy group is protected, or a salt thereof.

11. A pharmaceutical comprising the 2-aminopropane-1,3-diol compound according to claim 2, a pharmaceutically acceptable acid addition salt thereof or a hydrate thereof.

12. An immunosuppressant comprising, as an active ingredient, the 2-aminopropane-1,3-diol compound according to claim 2, a pharmaceutically acceptable acid addition salt thereof or a hydrate thereof.

13. A suppressant of rejection comprising, as an active ingredient, the 2-aminopropane-1,3-diol compound according to claim 2, a pharmaceutically acceptable acid addition salt thereof or a hydrate thereof.

14. An agent for the treatment of graft-versus-host diseases comprising, as an active ingredient, the 2-aminopropane-1,3-diol compound according to claim 2, a pharmaceutically acceptable acid addition salt thereof or a hydrate thereof.

15. An agent for the treatment of autoimmune diseases or allergic diseases comprising, as an active ingredient, the 2-aminopropane-1,3-diol compound according to claim 2, a pharmaceutically acceptable acid addition salt thereof or a hydrate thereof.

16. A pharmaceutical composition comprising, as an active ingredient, the 2-aminopropane-1,3-diol compound according to claim 2, a pharmaceutically acceptable acid addition salt thereof or a hydrate thereof, and a pharmaceutically acceptable carrier.

17. A compound according to claim 9, wherein the amino group is protected by an aliphatic acyl group, an aromatic acyl group, a carbonate group, a trityl group, a di- or trialkylsilyl group, a benzyl group, or a p-nitrobenzyl group.

18. A compound according to claim 17, wherein the aliphatic acyl group is selected from the group consisting of formyl, acetyl, propionyl, chloroacetyl, dichloroacetyl, trichloroacetyl, trifluoroacetyl, methanesulfonyl, and ethanesulfonyl; the aromatic acyl group is selected from the group consisting of phthaloyl, benzoyl, p-nitrobenzoyl, p-tert-butylbenzoyl, p-tert-butylbenzenesulfonyl, benzenesulfonyl, and toluenesulfonyl; and the carbonate group is selected from the group consisting of methoxycarbonyl, ethoxycarbonyl, isopropoxycarbonyl, tert-butoxycarbonyl, 2-cyanoethoxycarbonyl, 2,2,2-trichloroethoxycarbonyl, benzyloxycarbonyl, p-nitrobenzyloxycarbonyl, p-methoxybenzyloxycarbonyl, p-chlorobenzyloxycarbonyl, diphenylmethoxycarbonyl, methoxymethyloxycarbonyl, acetylmethyloxycarbonyl, phenyloxycarbonyl, methylsulfonylethyloxycarbonyl, and 2-trimethylsilylethoxycarbonyl.

19. A compound according to claim 10, wherein the amino group is protected by an aliphatic acyl group, an aromatic acyl group, a carbonate group, a trityl group, a di- or trialkylsilyl group, a benzyl group, or a p-nitrobenzyl group.

20. A compound according to claim 19, wherein the aliphatic acyl group is selected from the group consisting of formyl, acetyl, propionyl, chloroacetyl, dichloroacetyl, trichloroacetyl, trifluoroacetyl, methanesulfonyl, and ethanesulfonyl; the aromatic acyl group is selected from the group consisting of phthaloyl, benzoyl, p-nitrobenzoyl, p-tert-butylbenzoyl, p-tert-butylbenzenesulfonyl, benzenesulfonyl, and toluenesulfonyl; and the carbonate group is selected from the group consisting of methoxycarbonyl, ethoxycarbonyl, isopropoxycarbonyl, tert-butoxycarbonyl, 2-cyanoethoxycarbonyl, 2,2,2-trichloroethoxycarbonyl, benzyloxycarbonyl, p-nitrobenzyloxycarbonyl, p-methoxybenzyloxycarbonyl, p-chlorobenzyloxycarbonyl, diphenylmethoxycarbonyl, methoxymethyloxycarbonyl, acetylmethyloxycarbonyl, phenyloxycarbonyl, methylsulfonylethyloxycarbonyl, and 2-trimethylsilylethoxycarbonyl.

21. A compound according to claim 9, wherein the hydroxy group is protected by a substituted or unsubstituted lower alkyl group, an allyl group, a substituted or unsubstituted aralkyl group, a tri-substituted silyl group, a tetrahydropyranyl group, a tetrahydro-2-thiopyranyl group, a 2-thioalanyl group, or an acyl group.

22. A compound according to claim 21, wherein the substituted or unsubstituted lower alkyl group is selected from the group consisting of methyl, ethyl, propyl, butyl, tert-butyl, pentyl, hexyl, methoxymethyl, and methoxyethoxymethyl; the substituted or unsubstituted aralkyl group is selected from the group consisting of benzyl, p-methoxybenzyl, triphenylmethyl, and tris(p-methoxyphenyl)methyl; the tri-substituted silyl group is selected from the group consisting of trimethylsilyl, triethylsilyl, tert-butyldimethylsilyl, tri-tert-butylsilyl, methyldiphenylsilyl, ethyldiphenylsilyl, propyldiphenylsilyl, and tert-butyldiphenylsilyl; and the acyl group is selected from the group consisting of aliphatic acyl, aromatic acyl, and aliphatic acyl substituted by an aromatic group, which are derived from carboxylic acids and sulfonic acids.

23. A compound according to claim 10, wherein the hydroxy group is protected by a substituted or unsubstituted lower alkyl group, an allyl group, a substituted or unsubstituted aralkyl group, a tri-substituted silyl group, a tetrahydropyranyl group, a tetrahydro-2-thiopyranyl group, a 2-thioalanyl group, or an acyl group.

24. A compound according to claim 23, wherein the substituted or unsubstituted lower alkyl group is selected from the group consisting of methyl, ethyl, propyl, butyl, tert-butyl, pentyl, hexyl, methoxymethyl, and methoxyethoxymethyl; the substituted or unsubstituted aralkyl group is selected from the group consisting of benzyl, p-methoxybenzyl, triphenylmethyl, and tris(p-methoxyphenyl)methyl; the tri-substituted silyl group is selected from the group consisting of trimethylsilyl, triethylsilyl, tert-butyldimethylsilyl, tri-tert-butylsilyl, methyldiphenylsilyl, ethyldiphenylsilyl, propyldiphenylsilyl, and tert-butyldiphenylsilyl; and the acyl group is selected from the group consisting of aliphatic acyl, aromatic acyl, and aliphatic acyl substituted by an aromatic group, which are derived from carboxylic acids and sulfonic acids.

25. The compound of claim 1, wherein the acyl group at each of $R^1$, $R^2$, $R^3$, and $R^4$, is a straight or branched chain alkanoyl having 1 to 6 carbon atoms, a straight or branched chain alkanoyl having 2 to 6 carbon atoms which is substituted by phenyl, an aroyl, an alkoxycarbonyl wherein the alkoxy moiety is a straight or branched chain alkoxy having 1 to 6 carbon atoms, and an aralkyloxycarbonyl.

26. The compound of claim 25, wherein the straight or branched chain alkanoyl having 1 to 6 carbon atoms is selected from the group consisting of formyl, acetyl, propionyl, butyryl, isobutyryl, pentanoyl, and hexanoyl; the straight or branched chain alkanoyl having 2 to 6 carbon atoms which is substituted by phenyl is selected from the group consisting of phenylacetyl and phenylpropionyl; the aroyl is benzoyl; the alkoxycarbonyl wherein the alkoxy moiety is a straight or branched chain alkoxy having 1 to 6 carbon atoms is selected from the group consisting of methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, tert-pentyloxycarbonyl, and hexyloxycarbonyl; and the aralkyloxycarbonyl is benzyloxycarbonyl.

27. A method of suppressing rejection in organ or bone marrow transplantation, comprising administering a rejection-suppressing-effective amount of the composition of claim 8.

28. A method of suppressing rejection in organ or bone marrow transplantation, comprising administering a rejection-suppressing-effective amount of the composition of claim 16.

29. A method according to claim 28, wherein the composition is administered orally or parenterally.

30. A method of treating autoimmune diseases, comprising administering an effective amount of the composition of claim 8.

31. A method of treating autoimmune diseases according to claim 30, wherein said autoimmune diseases are selected from the group consisting of atopic dermatitis, psoriasis, articular rheumatism, and Beçcet's disease.

32. A method of treating autoimmune diseases, comprising administering an effective amount of the composition of claim 16.

33. A method of treating autoimmune diseases according to claim 32, wherein said autoimmune diseases are selected from the group consisting of atopic dermatitis, psoriasis, articular rheumatism, and Behçet's disease.

34. A method according to claim 30, wherein the composition is administered orally, parenterally, or topically.

35. A method according to claim 34, wherein the composition is administered in an amount to provide a dose of said active ingredient of 0.01–50 mg/person/day for parenteral administration by a subcutaneous, intravenous, or intramuscular route, or for topical administration through the skin, eye, lung, bronchus, nose, or rectum, and a dose of about 0.01–150 mg/person/day for oral administration.

36. A method according to claim 35, wherein said dose for parenteral administration is 0.01–20 mg/person/day, and said dose for oral administration is 0.1–100 mg/person/day.

37. A method according to claim 31, wherein the composition is administered orally, parenterally, or topically.

38. A method according to claim 37, wherein the composition is administered in an amount to provide a dose of said active ingredient of 0.01–50 mg/person/day for parenteral administration by a subcutaneous, intravenous, or intramuscular route, or for topical administration through the skin, eye, lung, bronchus, nose, or rectum, and a dose of about 0.01–150 mg/person/day for oral administration.

39. A method according to claim 38, wherein said dose for parenteral administration is 0.01–20 mg/person/day, and said dose for oral administration is 0.1–100 mg/person/day.

40. A composition according to claim 8, in the form of an ointment or a lotion.

41. A composition according to claim 40, comprising 0.01–10 w/w % of said active ingredient and a pharmaceutically acceptable base in the case of an ointment or liquid medium in the case of a lotion.

42. A composition according to claim 16, in the form of an ointment or a lotion.

43. A composition according to claim 42, comprising 0.01–10 w/w % of said active ingredient and a pharmaceutically acceptable base in the case of an ointment or liquid medium in the case of a lotion.

44. A composition according to claim 8, in the form of an eye drop or nasal drop.

45. A composition in the form of an eye drop according to claim 44, comprising 0.01–2.0 w/v % of said active ingredient and a pharmaceutically acceptable solvent, at a pH of about 4.0 to about 8.5.

46. A composition according to claim 16, in the form of an eye drop or nasal drop.

47. A composition in the form of an eye drop according to claim 46, comprising 0.01–2.0 w/v % of said active ingredient and a pharmaceutically acceptable solvent, at a pH of about 4.0 to about 8.5.

48. A method of treating eye inflammation comprising administering an anti-inflammation-effective amount of the composition of claim 45.

49. A method of treating eye inflammation comprising administering an anti-inflammation-effective amount of the composition of claim 47.

50. A method according to claim 48, comprising administering said composition 1 to 4 times per day in a sufficient amount of said composition to provide a dose of 5.0–1000 μg of said active ingredient per administration.

51. A method according to claim 49, comprising administering said composition 1 to 4 times per day in a sufficient amount of said composition to provide a dose of 5.0–1000 μg of said active ingredient per administration.

* * * * *